US010252268B2

(12) United States Patent
Linbeck, III et al.

(10) Patent No.: US 10,252,268 B2
(45) Date of Patent: *Apr. 9, 2019

(54) AUTOMATED DRIVING OF AN ASSAY

(71) Applicant: fannin partners llc, Houston, TX (US)

(72) Inventors: Leo Linbeck, III, Houston, TX (US);
Michael John Heffernan, Katy, TX (US); Dev Chatterjee, Saint Louis, MO (US)

(73) Assignee: Fannin Partners LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/390,650

(22) Filed: Dec. 26, 2016

(65) Prior Publication Data

US 2017/0102384 A1 Apr. 13, 2017

Related U.S. Application Data

(63) Continuation-in-part of application No. 14/992,370, filed on Jan. 11, 2016, now Pat. No. 9,528,985, which
(Continued)

(51) Int. Cl.
*G01N 33/543* (2006.01)
*B01L 3/00* (2006.01)
*G01N 21/78* (2006.01)

(52) U.S. Cl.
CPC ... *B01L 3/502761* (2013.01); *B01L 3/502784* (2013.01); *G01N 21/78* (2013.01);
(Continued)

(58) Field of Classification Search
CPC ....... G01N 33/54386; G01N 33/54326; G01N 21/78; G01N 33/54333; B01L 3/502761;
(Continued)

(56) References Cited

U.S. PATENT DOCUMENTS 6,254,826 B1 * 7/2001 Acosta ............... B01L 3/02
422/561
8,691,149 B2 * 4/2014 Fritchie ............. B01L 3/0289
210/222
(Continued)

*Primary Examiner* — Benjamin R Whatley
(74) *Attorney, Agent, or Firm* — Eric P. Mirabel, JD, LLM

(57) ABSTRACT

The invention herein relates to conducting assays with an apparatus including a substantially transparent assay cartridge loaded with magnetic beads, and a magnet carrier base positioned below a scanning platform holding the assay cartridge. The assay cartridge includes magnetic beads, sample and control solutions in some wells, and assay reagents in others. A microcomputer controls a DC motor which controls movement of the magnet carrier base, and causes the magnetic beads to travel from one well to another. An electromagnetic coil-spring assembly induces mixing of well contents with the magnetic beads on actuation. The assay cartridge is authenticated by sending its encoding to a server or website, and assay instructions are provided remotely to the microcomputer. Following assay completion, the cartridge can have color change or other assay indication detected, and the results sent to the server or website or another recipient.

20 Claims, 21 Drawing Sheets

Related U.S. Application Data is a continuation-in-part of application No. PCT/US2015/013097, filed on Jan. 27, 2015.

(60) Provisional application No. 62/412,734, filed on Oct. 25, 2016, provisional application No. 61/932,200, filed on Jan. 27, 2014.

(52) U.S. Cl.
CPC .. *G01N 33/54333* (2013.01); *B01L 2200/027* (2013.01); *B01L 2200/0668* (2013.01); *B01L 2200/0673* (2013.01); *B01L 2300/021* (2013.01); *B01L 2300/087* (2013.01); *B01L 2300/0816* (2013.01); *B01L 2300/0858* (2013.01); *B01L 2300/0864* (2013.01); *B01L 2400/043* (2013.01)

(58) Field of Classification Search
CPC ......... B01L 3/502784; B01L 2200/027; B01L 2200/0668; B01L 2200/0673; B01L 2300/021; B01L 2300/0816; B01L 2300/0858; B01L 2300/0864; B01L 2300/087; B01L 2400/043
USPC .......................................................... 422/67
See application file for complete search history.

(56) References Cited

U.S. PATENT DOCUMENTS

| | | | |
|---|---|---|---|
| 2004/0157336 A1* | 8/2004 | Petroff | B01L 9/527 436/47 |
| 2009/0325274 A1 | 12/2009 | Hamada | |
| 2011/0008813 A1* | 1/2011 | Dilleen | B01L 3/502715 435/28 |
| 2012/0178096 A1* | 7/2012 | Beebe | G01N 33/543 435/6.19 |
| 2013/0209334 A1* | 8/2013 | Wilson | B01L 3/50825 422/554 |

* cited by examiner

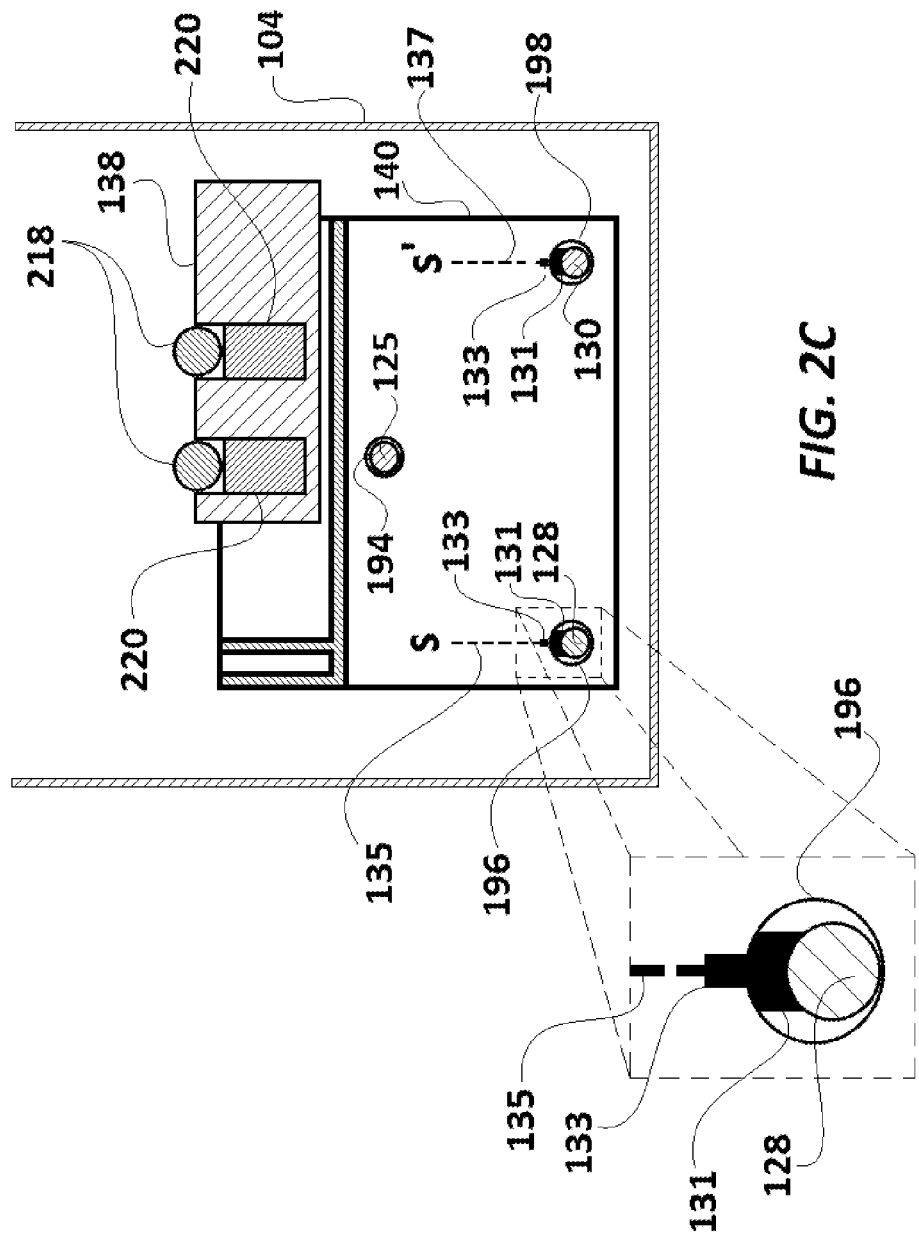

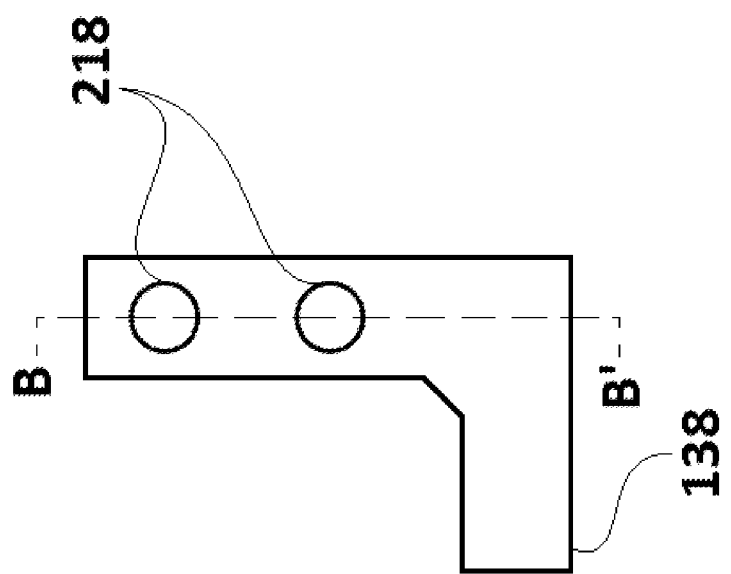

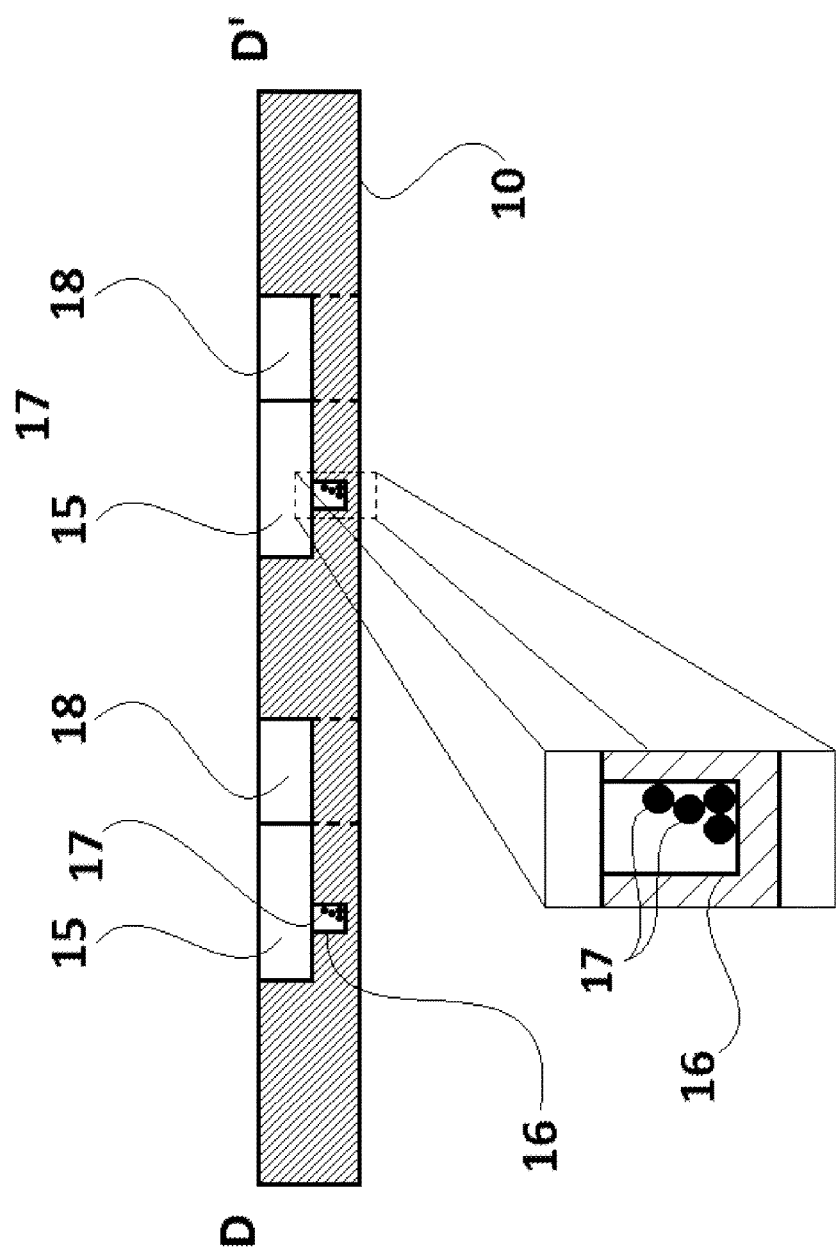

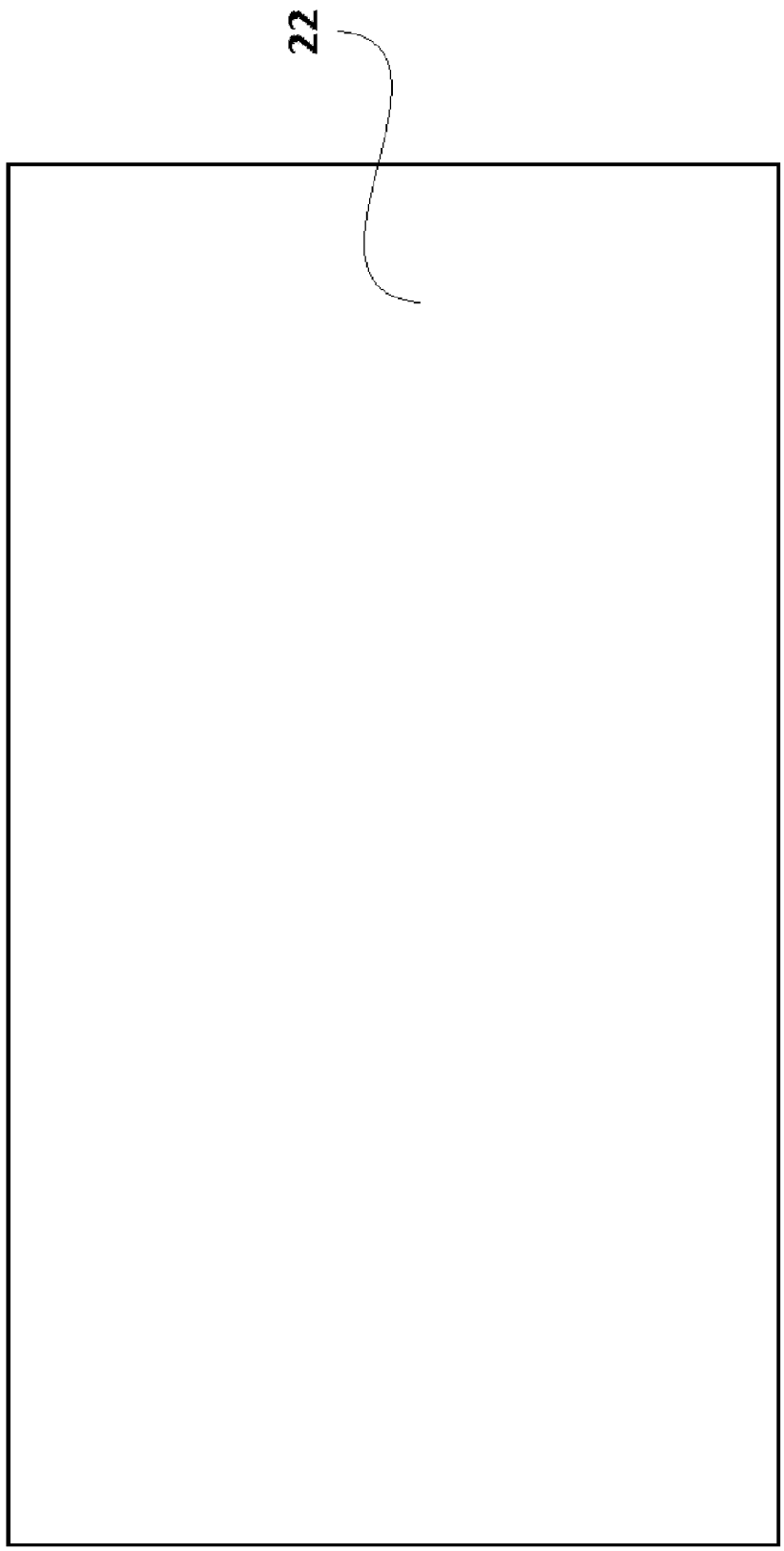

AUTOMATED DRIVING OF AN ASSAY

GOVERNMENTAL RIGHTS

This invention was made with governmental support under Grant Number 1R43DA041966-01, awarded by the National Institute on Drug Abuse. The government has certain rights in the invention.

BACKGROUND

A reliable, robust assay system which can be deployed to a point of care is useful in a number of settings. For example, where there is an infectious disease outbreak in a remote area (e.g., the recent Ebola outbreaks), such an assay is of benefit for arresting the outbreak as quickly as possible (infected individuals can be quickly located then isolated) and for keeping health care providers safer.

An assay driver system can be used to automate an assay. One type of assay driver induces movement of magnetic beads which contact sample (or control) and then carry it into contact with assay reagents. The movement has to be carefully timed, to ensure proper reaction times in different reagents. The results must also be readable for fast interpretation. One type of discontinuous point of care assay system suitable for use with an assay driver herein is disclosed in US Publ'n No. 2016/0195523 (incorporated by reference). This application discloses a cartridge having wells containing various assay reagents. Magnetic beads also reside in the wells, and the magnetic beads are moved among the wells in order to carry sample into contact with different assay reagents in different wells.

An assay driver system can be used to automate the assay, by moving magnets (and carrying the magnetic beads) through the wells of the cartridge, and into contact with the assay reagents in various wells. The movement has to be carefully timed, to ensure proper reaction times in different reagents. The results must also be read and sent for interpretation, and to permit quick action. No current system automates these functions. Remote authentication of the cartridge (to provide the proper instructions to the driver) and automation of the individual assays which can be performed by the cartridge, coupled with reading and sending of assay results from the point of care is needed, to solve the problems associated with a rapidly spreading infection.

In currently known assay driver systems the movement of magnetic beads has to be carefully timed to ensure proper reaction times between them and different reagents. Additionally, during mixing of the beads with the reagents in wells of an assay cartridge, an appropriate magnetic field and movement of it has to be applied to prevent clustering of beads while they are being moved. Clustering prevents proper mixing of the beads with the reagents in the wells. Hence there is a need for an improved automated assay driver system which is more accurate, more efficient, is less vulnerable to inaccuracies and facilitates faster interpretation of assay results.

SUMMARY

The invention is an apparatus and method for performing an assay where a sample or binding agent or antigen, carried by magnetic beads, is brought in contact with different assay reagents in different wells of an assay cartridge. The movement of magnetic beads among wells of the cartridge is driven and guided by controlled movement of magnets or a magnetic array, preferably including scanning magnets and corresponding orienting magnets, though other means of generating magnetic force, including electromagnets, could be used. The movement of the magnets is controlled by an apparatus in accordance with a set of authenticated assay instructions.

In one embodiment the apparatus comprises a substantially transparent assay cartridge, a scanning platform for the assay cartridge, an array of magnets installed on a magnet carrier base, two metallic rail rods installed parallel to a first axis, an externally threaded driving rod lying parallel to the first axis, and an electromagnetic inducing coil. The array of magnets preferably further comprises a plurality of spherical scanning magnets which are oriented to align with the poles in the proper orientation using a corresponding cylindrical orienting magnet for each scanning magnet. Each orienting magnet lies vertically, with one pole at the top, and aligned below its corresponding scanning magnet. The orienting magnets can be fixed, but the spherical magnets can move in their holder enough to such that the poles align the same way as the poles of the orienting magnets. The magnet carrier base resides under the scanning platform.

The assay cartridge preferably includes magnetic beads, sample and control in two of its wells, and assay reagents in others. The magnet carrier base is positioned a specific distance below the scanning platform (having the assay cartridge placed on it) such that the magnetic beads in the assay cartridge experience a defined magnitude of magnetic field (provided by scanning magnets and orienting magnets). The magnet carrier base is movable with respect to the assay cartridge along a first axis and a second axis, wherein the first axis intersects the second axis, and wherein movement of the magnet carrier base along the first axis is powered by rotation of an externally threaded driving rod which extends through a mating threaded portion of the magnet carrier base. Rotation of the externally threaded driving rod is driven by the shaft of a DC motor.

While moving along the first axis, the magnet carrier base also slides on two rail rods which extend through the magnet carrier base. The two rail rods prevent skewing of the magnet carrier base while moving along the first axis. Further, the two rail rods may also be in electrical contact with the electromagnet coil which, when actuated by applying electrical potential difference across the rods, moves the magnet carrier base along the second axis. A compressible spring provided with the magnet carrier base causes the magnet carrier base to return rapidly back along the second axis when the coil is de-actuated or when the potential across the two rail rods is substantially reduced from the actuating potential.

To automate the movement of the magnet carrier base (and the array of magnets) within a predefined two-dimensional space defined by the lengths of the first and the second axes, the device is further equipped with a microcomputer. The microcomputer controls the operations of the DC motor, and varies the levels of electrical potential difference across the two rail rods. The microcomputer is powered by a DC power source included in the device.

To conduct an assay, a loaded assay cartridge (preferably having a sample, control, magnetic beads and reagents loaded in wells) is placed on the scanning platform and based on a barcode identity of the assay cartridge, the cartridge identity is authenticated and a set of assay instructions are sent. The microprocessor drives and guides movement of the magnet carrier base (and the array of magnets) by executing the instructions. The magnetic beads follow movement of the scanning platform, and travel from one well to another to interact with different reagents in performance of the assay.

Embodiments of the invention are discussed in greater detail with reference to the accompanying figures in the detailed description which follows.

BRIEF DESCRIPTION OF DRAWINGS

FIG. 2C illustrates a sectional view taken along the lines B-B of FIG. 2A.

FIG. 2D is a magnified view of a portion of FIG. 2A, indicated by the dotted lines.

FIG. 4A is a plan view of the magnet carrier base of the driving box of FIG. 2.

FIG. 5F illustrates a cross-sectional view of assay cartridge base of FIG. 5B taken along lines D-D'.

FIG. 5G illustrates a magnified view of one of the mini-wells 16 showing microbeads 17.

FIG. 6D illustrates a plan view of the assay cartridge with the cover in place.

Figure 1:
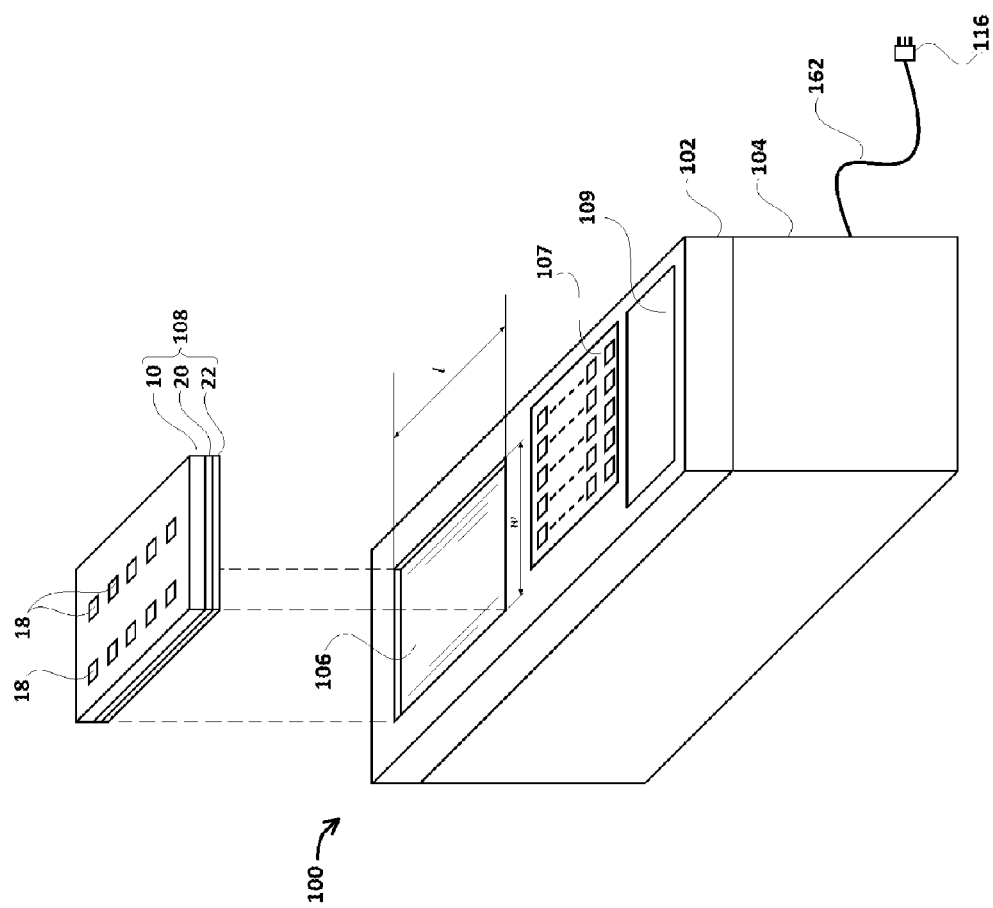
FIG. 1 illustrates a perspective view of the driving box of an embodiment of the assay driving apparatus of the invention.

It should be understood that the drawings and the associated descriptions below are intended only to illustrate one or more embodiments of the present invention, and not to limit the scope of the invention. The drawings are not necessarily to scale.

DETAILED DESCRIPTION

The term "magnetic beads" refers to bead-shaped objects of any size (including microbeads) and composition which can be attracted or repulsed by a magnetic force, including objects containing paramagnetic materials or magnetizable materials, such as conductors, and including conductive metals.

Reference will now be made in detail to a first embodiment of an assay device of the invention with reference to the accompanying FIGS. 1-7. As illustrated in these figures, assay device 100 comprises a scanner cover 102 and a driving box 104. The scanner cover 102 serves as a cover for the driving box 104 and includes a scanning platform 106 where a loaded assay cartridge 108 is placed for scanning (either or both, before and following the assay, see below). The term 'loaded assay cartridge' is meant designate an assay cartridge which is filled or loaded with some or all of a sample ready to be analyzed, a control and magnetic beads The loaded assay cartridge 108 is shown as covered with layer 20 and cover 22.

Scanner cover 102 also includes a keyboard 107 and a display 109, as well as a scanner (not illustrated) for capturing scanned images of the loaded assay cartridge 108, when it is placed on scanning platform 106. The scanner would capture images of loaded assay cartridge 108 from the upper side (in FIG. 1), because the view of the lower side is obstructed by cover 22.

Driving box 104 includes a first compartment 110, a second compartment 112, a third compartment 114, an AC power source 116, an AC power supply switch 118, AC-to-DC converter section 120, a DC motor 122, a partially threaded metallic driving shaft 124 of the DC motor 122, a metallic threaded driving rod 125, a metallic coupling cylinder 126, a first rail rod 128, a second rail rod 130, a solenoid 132, a solenoid shaft 134, a compressible spring 136, a magnet carrier base 138, a holding structure 140, a microcomputer 142, insulated electric conductor wires 144, 146, 148, 150, 152, 154, 156, 158, and 160, and an AC power cord 162. The first compartment 110 and the second compartment 112 are separated by a common wall 164, and the second compartment 112 and the third compartment 142 are separated by a common wall 166.

While the solenoid 132, the solenoid shaft 134, the compressible spring 136, the magnet carrier base 138, and the holding structure 140 lie in a first compartment 110, the AC-to-DC converter section 120, the coupling cylinder 126, and the microcomputer 142, lie in the second compartment 112. The DC motor 122 lies in the third compartment 114.

Figure 2A:
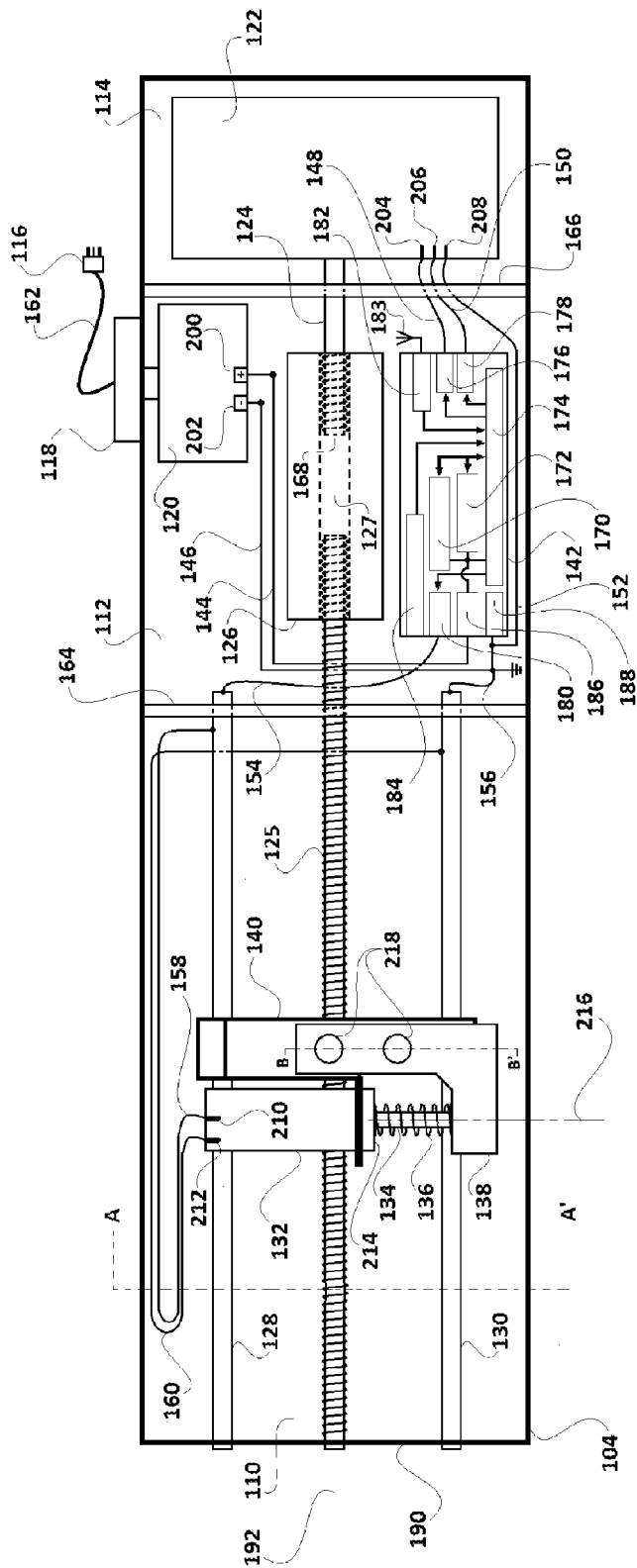
FIG. 2A illustrates a perspective view from above, showing the insides of the driving box of FIG. 1, with its upper cover (i.e. scanner cover) removed.

FIG. 2A illustrates an embodiment where wires 158 and 160 are connected, respectively, with first and second rail rods 128 and 130 which are made of electrically conductive material (preferably a metal) and are laid bare (i.e. without an insulation cover) within the driving box 104. One could also connect wires 158 and 160 directly with microcomputer 142, instead of to rail rods 128 and 130. Other means of electrically connecting solenoid 132 with a power source are intended to be included within the scope of the invention. For example, instead of being powered through insulated conductor wires 158 and 160 (FIG. 2A), the inputs 210 and 212 of solenoid 132 can be connected to the first and second rail rods 128 and 130 through two separate brushes which make sliding contact, as shown in FIGS. 2B to 2F. In another embodiment, instead of wires 158, 160 or brushes as in FIG. 2B, one could attach conductive tape to the inside wall of a driving box 104, and have brushes extending from holding structure 140 which make contact to form an electrical connection between the conductive tape and solenoid 132. In another embodiment best seen in FIGS. 2E and 2F, rail rods 128 and 130 are formed with at least one substantially horizontal surface including with a rectangular cross-section as shown.

It is noted that in the embodiments shown in FIGS. 2B to 2F, brush 131 with bristles 135 sit in port 133, residing in holding structure 140. Port 133 encompasses electrical mating of brush 131 and connecting wires 135 and 137 (dotted lines). Ends S and S' of the connecting wires 135 and 137 get connected to input of solenoid 132 (not illustrated).

Figure 2B:
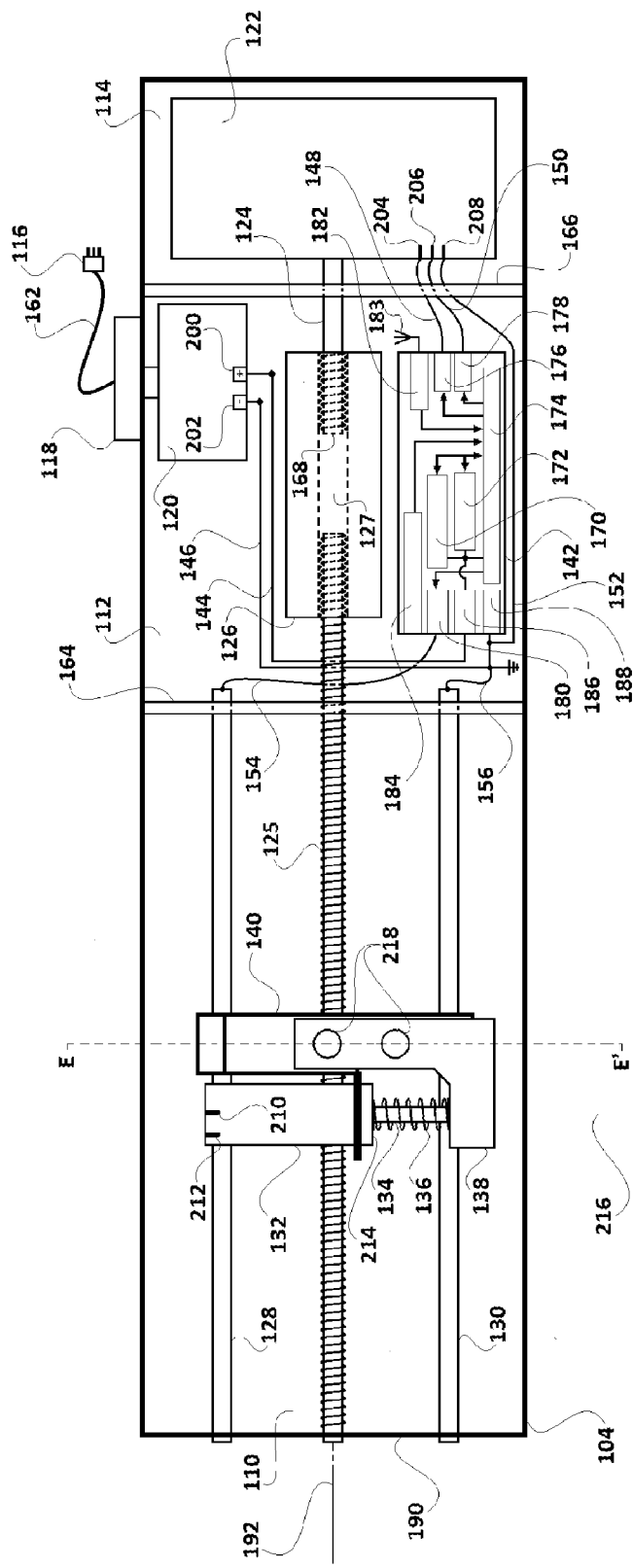
FIG. 2B is the same view as in FIG. 2A, but of a different embodiment with a different mode of electrical connection from a microcomputer to a solenoid.
Figures 2E, 2F:
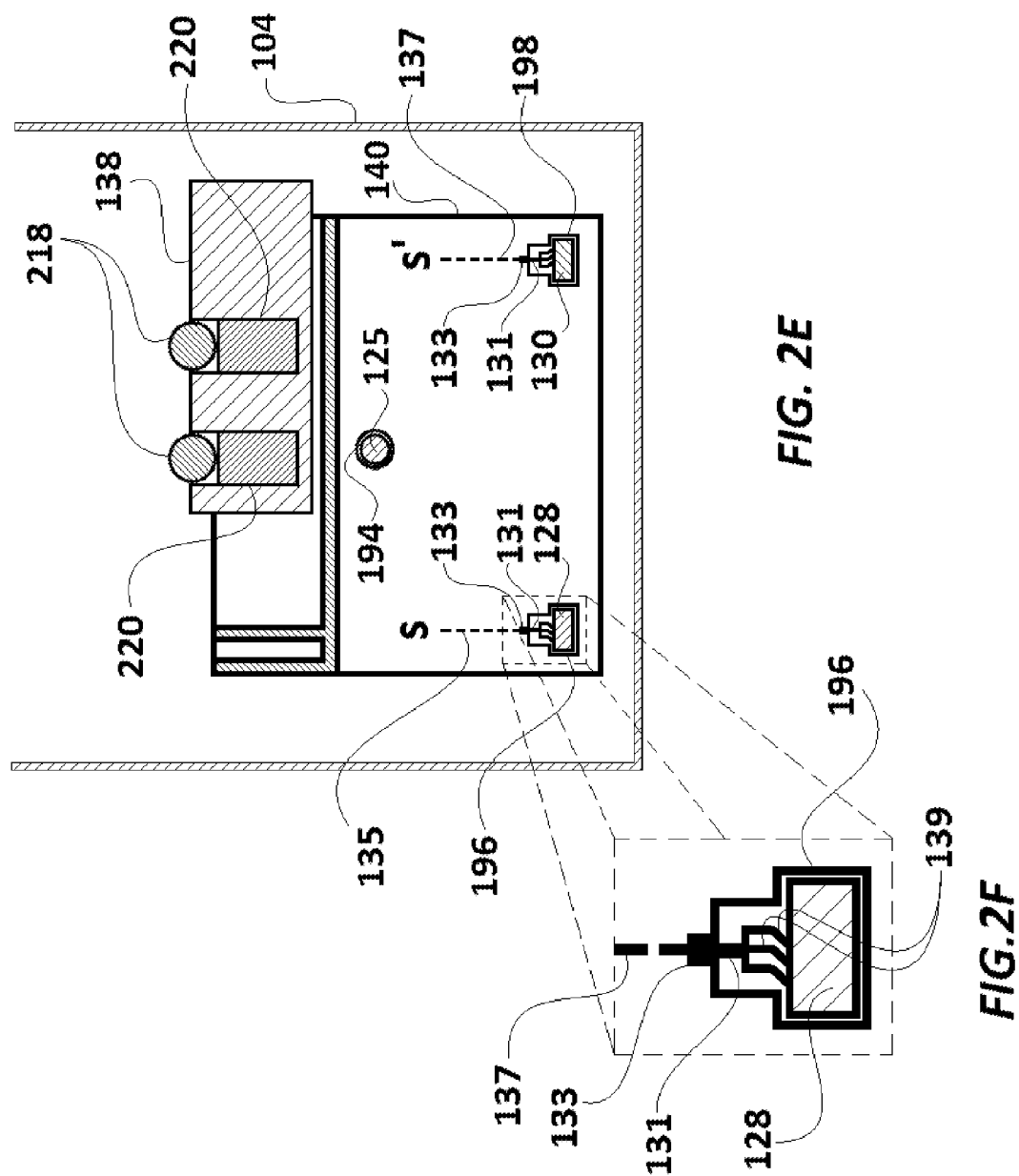
FIG. 2E is a sectional view taken along the lines E-E of FIG. 2B.
FIG. 2F is a magnified view of a portion of FIG. 2B, indicated by the dotted lines.
Figure 3:
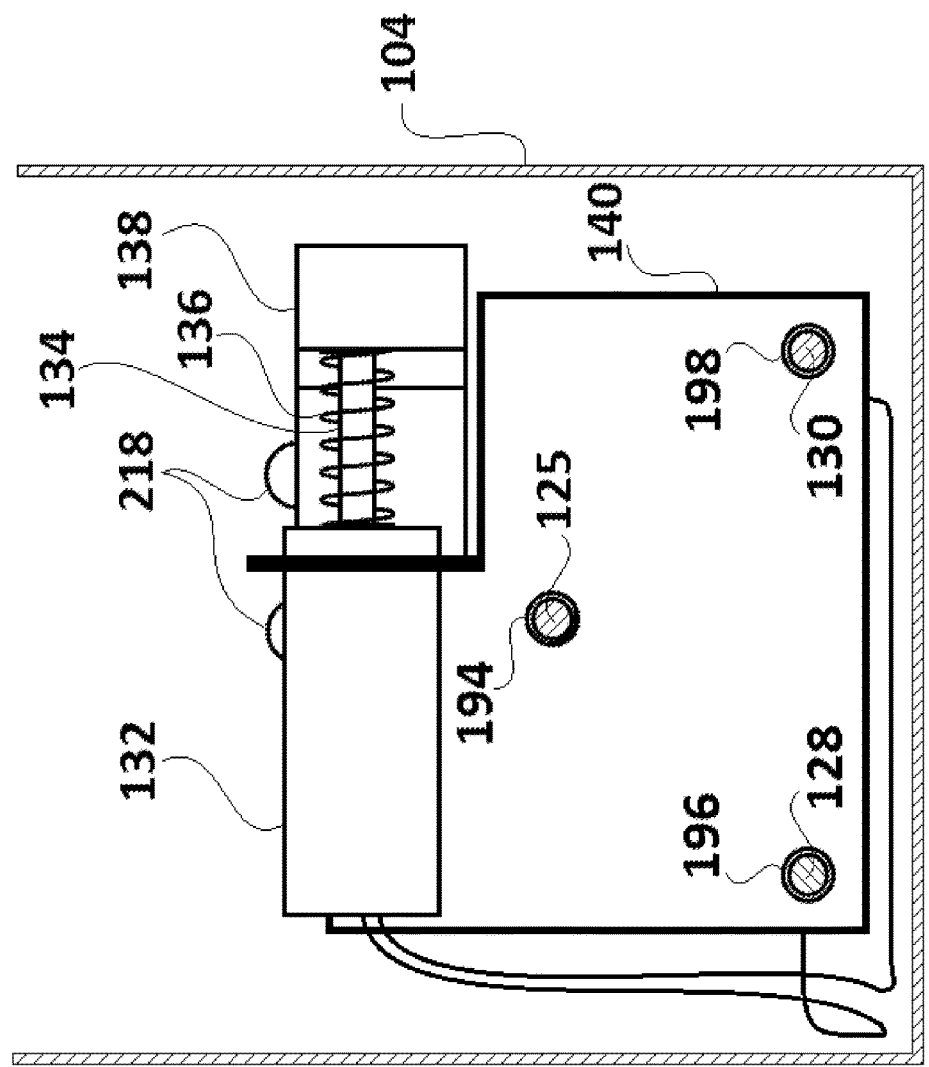
FIG. 3 is a cross-sectional view of the driving box of FIG. 2 taken along a line A-A'.

Referring to FIGS. 2A and 2B, first and second rail rods 128 and 130, as well as threaded driving rod 125, extend through the first compartment 110 into the second compartment 112. The partially threaded metallic driving shaft 124 extends through the third compartment 114 into second compartment 112. The externally threaded end 168 of the partially threaded metallic driving shaft 124 lies in the second compartment 112.

Coupling cylinder 126 couples the partially threaded metallic driving shaft 124 and the threaded driving rod 125 and keeps them aligned along a common axis 192. A longitudinal bore 127 which extends through the coupling cylinder 126 is threaded internally at both ends. One end of the threaded driving rod 125 and the externally threaded end 168 of the partially threaded metallic driving shaft 124 are screwed into the bore 127 form its opposite ends. In alternative embodiments, other means to couple the threaded driving shaft 124 and the externally threaded end 168 with the coupling cylinder 126 may be used. For example, instead of screwing in the threaded driving shaft 124 and the externally threaded end at either end of the coupling cylinder 126, both of them may be welded into the coupling cylinder 126, or mechanically joined with gears and sprockets.

The microcomputer 142 includes a CPU 170, memory 172, Input/Output subsystem 174 (hereinafter referred as I/O subsystem 174), first output port 176, second output port 178, third output port 180, a transceiver unit 182 (having a transceiver antenna 183), an operator input section 184, a DC voltage input port 186 and an electric ground connection port 188. The microcomputer 142 gets electrical power from DC voltage input port 186. An optional operator input section 184 of microcomputer 142 receives user instructions from the keyboard 107 provided on the scanner cover 102. The keyboard 107 is also used to instruct the scanner included in the scanner cover 104 to perform image scans of the loaded assay cartridge 108, following assay completion.

Optional external inputs to microcomputer 142 from external memory devices (such as flash memories) are connectable to the microcomputer 142 through ports (such as USB ports, not illustrated) can be included. Further, wireless inputs (for example, to receive instructions from a remote server) can also be provided for microcomputer 142 through the transceiver unit 182. When instructed (either wirelessly or otherwise automatically, or manually through keyboard 107), the transceiver unit 182 can wirelessly transmit data generated by assay device 100 (such as assay data or scanned images of the assay cartridge 108) to intended destinations, such as to an associated server. Further, transceiver unit 182 also facilitates wireless communication with associated external devices (such as servers and wireless handheld devices), see FIG. 7.

Microcomputer 142 generates executable instructions/outputs from the first output port 176, second output port 178, and the third output port 180, and receives and transmits data from the transceiver unit 182. The display 109 is connected to the keyboard 107, the scanner and to the microcomputer 142. The display 109 provides the user with visual interface to the device 100.

As a result of the coupling provided at the coupling cylinder 126, when the threaded driving shaft 124 is rotated by the DC motor 122, the coupling cylinder 126 and the threaded driving rod 125 also rotate in the same direction. Though longitudinal displacement of the driving shaft 124 along its longitudinal axis 192 is limited by the supports at either end, both supports are designed such that the driving shaft 124 is rotatable around the longitudinal axis 192. Similarly, the longitudinal displacement of the threaded driving rod 125 along its longitudinal axis 192 is limited by its supports at wall 190 and coupling cylinder 126. Both supports are designed such that the threaded driving rod 125 is rotatable around the longitudinal axis 192.

The DC motor 122, the driving shaft 124, the threaded driving rod 125 and the coupling cylinder 126 are installed within the driving box 104 such that the axis 192 divides the driving box 104 into two equal and symmetrical halves. The ends of the first rail rod 128 and the second rail rod 130 are supported on the common wall 164 and wall 190. The first rail rod 128, and the second rail rod 130 are fixed with the walls 164 and 190 in a manner such that they can't be displaced or rotated. Further, the first rail rod 128 and the second rail rod 130 lie parallel to axis 192. Along their longitudinal span, the driving shaft 124 and the threaded driving rod 125 pass through corresponding circular apertures made in walls 166 and 164 respectively. The corresponding circular apertures of walls 166 and 164 have a larger diameter than the driving shaft 124 and the threaded driving rod 125 respectively. Since the peripheries of circular apertures of walls 166 and 164 do not lie in contact with the corresponding driving shaft 124 or the threaded driving rod 125, they do not hinder rotational motion of the driving shaft 124 or the threaded driving rod 125 around the longitudinal axis 192.

In the first compartment 110, the first rail rod 128, the second rail rod 130 and the threaded driving rod 125 pass through the holding structure 140. While an internally threaded circular aperture 194 (illustrated in FIG. 3) of the holding structure 140 is screwed together with the threaded driving rod 125, the holding structure 140 slidably rests on the first rail rod 128 and the second rail rod 130 which pass through it at aperture 196 and aperture 198, respectively. Functionally, when the threaded driving rod 125 is rotated in a first (e.g. clockwise) direction, due to rotation of the driving shaft 124 by the DC motor 122 in the first (e.g. clockwise) direction, the holding structure 140 (which is screwed with the threaded driving rod 125) slides over the first rail rod 128 and the second rail rod 130 and moves longitudinally towards the second compartment 112. Similarly, when the threaded driving rod 125 is rotated by the DC motor 122 in the opposite direction, the holding structure 140 slides over the first rail rod 128 and the second rail rod 130 and moves longitudinally towards wall 190 (i.e. away from the second compartment 112). Rail rods 128 and 130 prevent holding structure 140 from being skewed to one side or the other, by the forces exerted by the threaded driving rod 125 during travel.

The assay device 110 is powered by the AC-to-DC converter section 114. The AC-to-DC converter section 114 receives AC power supply from domestic AC power source 116 (for example, 110V, 60 Hz AC in the USA) through a power cord 162 and provides a 12V DC supply at its output ports 200 and 202. To achieve this conversion, AC-to-DC converter section 114 is equipped with necessary components and circuitry (such as step-down transformer, rectification, filter, voltage regulation and over voltage/spike protection circuits) so electric potential of port 200 is a constant 12V higher than port 202.

It is noted that though the present embodiment is powered by 12V DC supply, some embodiments of the invention may be powered with different DC voltages based on installed circuitry and components, or by DC batteries. Still further, for those embodiments of the invention which obtain DC supply by conversion of an AC power supply, the electrical circuitry for AC-DC conversion can be tailored in accordance with the type of AC power supply available at the location of usage and the desired magnitude of DC supply. For example, if an embodiment of the invention were to be used in the USA, the electrical circuitry for AC-DC conversion can be tailored in accordance with an available type of AC power supply of 110V-60 Hz, to achieve the desired magnitude of DC supply. For use in India, the electrical circuitry for AC-DC conversion can be tailored in accordance with an available type of AC power supply of 230V-50 Hz, and the desired magnitude of DC supply. Hence, all modifications in the circuitry of the device, or other modifications, to provide a desired level of DC supply from an available parent power source (such as AC power supply or battery/ies) are within the scope of the invention Returning to the current embodiment of the invention, microcomputer 142 is powered by connecting its corresponding DC power input port 186 and grounding port 188 with ports 200 and 202 respectively. While port 186 is connected to port 200 by insulated conductor wire 144, the grounding port 188 is connected to port 202 by insulated conductor wire 146. The first output port 176 and the second output port 178 of the microcomputer 142 are connected to power supply ports 204 and 206 of the DC motor 122 respectively. The first output port 176 is connected to power supply port 204 through insulated conductor wire 148, and the second output port 178 is connected to power supply port 206 through insulated conductor wire 150. The port 208 of the DC motor 122 is connected to grounding port 188 of the microcomputer 142 through insulated conductor wire 152. The operation of the first output port 176 and the second output port 178 is controlled by the microcomputer 142 and they can be kept either in disabled or enabled state by the microcomputer 142.

To drive the DC motor 122, either of the ports 204 or 206 are enabled by the microcomputer 142. When power supply port 204 is enabled (keeping port 206 disabled), the DC motor 122 is powered to rotate driving shaft 124 in a first (or clockwise) direction, and when power supply port 206 is enabled (keeping port 204 disabled), the DC motor 122 is powered to rotate driving shaft 124 in the opposite (counter-clockwise) direction. Any rotation of the driving shaft 124 in either direction would also drive the threaded driving rod 125. In the current embodiment, the enabling of either of ports 204 and 206 leads to application of potential difference of 9V DC with respect to the port 208.

The third output port 180 of the microcomputer 142 is connected the first rail rod 128 through insulated conductor wire 154. The second rail rod 130 is connected to the grounding port 188 through insulated conductor wire 156.

The operation of the third output port 180 is also controlled by the microcomputer 142. The third output port 180 can either be kept disabled or can be enabled at various DC voltage levels (preferably ranging between 2-9V) by the microcomputer 142. Based on the enabled DC voltage level provided by the microcomputer 142 at the third output port 180, an electric potential difference, preferably varying between 2-9 V DC, can be developed across first rail rod 128 and the second rail rod 130. The first rail rod 128 is further connected to an input 210 of the solenoid 132 through insulated conductor wire 158, and the second rail rod 130 is further connected to the inputs 212 of the solenoid 132 through insulated conductor wire 160

Input ports 210 and 212 are connected to ends of an electromagnet coil (not illustrated) included in the solenoid 132. In an unenergized state of the electromagnet coil (or when the third output port 180 is kept disabled by microcomputer 142), one end of the solenoid shaft 134 lies fully within the solenoid 132. The other end of the solenoid shaft 134 lies exterior to the solenoid 132 and is connected to magnet carrier base 138. The solenoid shaft 134 can made of a ferromagnetic magnetic material (such as iron). A compressible spring 136 surrounds the length of the solenoid shaft 134 lying exterior to the solenoid 132. As illustrated, the compressible spring 136 is placed between an end 214 of the solenoid 132 and the magnet carrier base 138. Though the solenoid shaft 134 is movable longitudinally along its axis 216 (axis 216 being perpendicular to the axis 192), its assembly with the solenoid 132 prevents its ejection from solenoid 132.

Figure 4B:
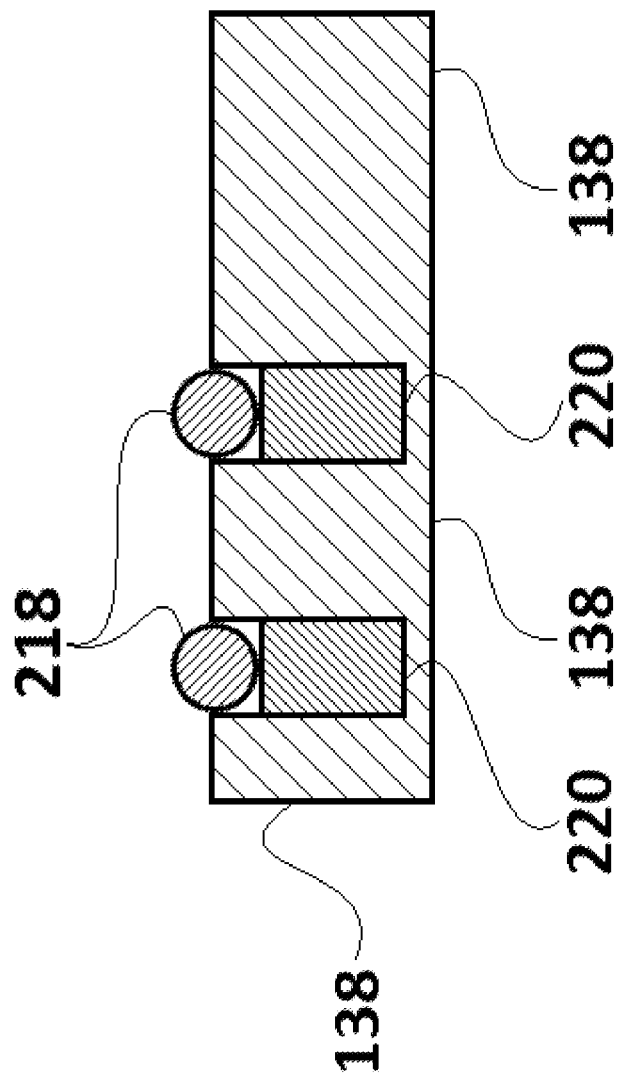
FIG. 4B is a cross-sectional view of the magnet carrier base of FIG. 4A, taken along a line B-B'.
Figure 5A:
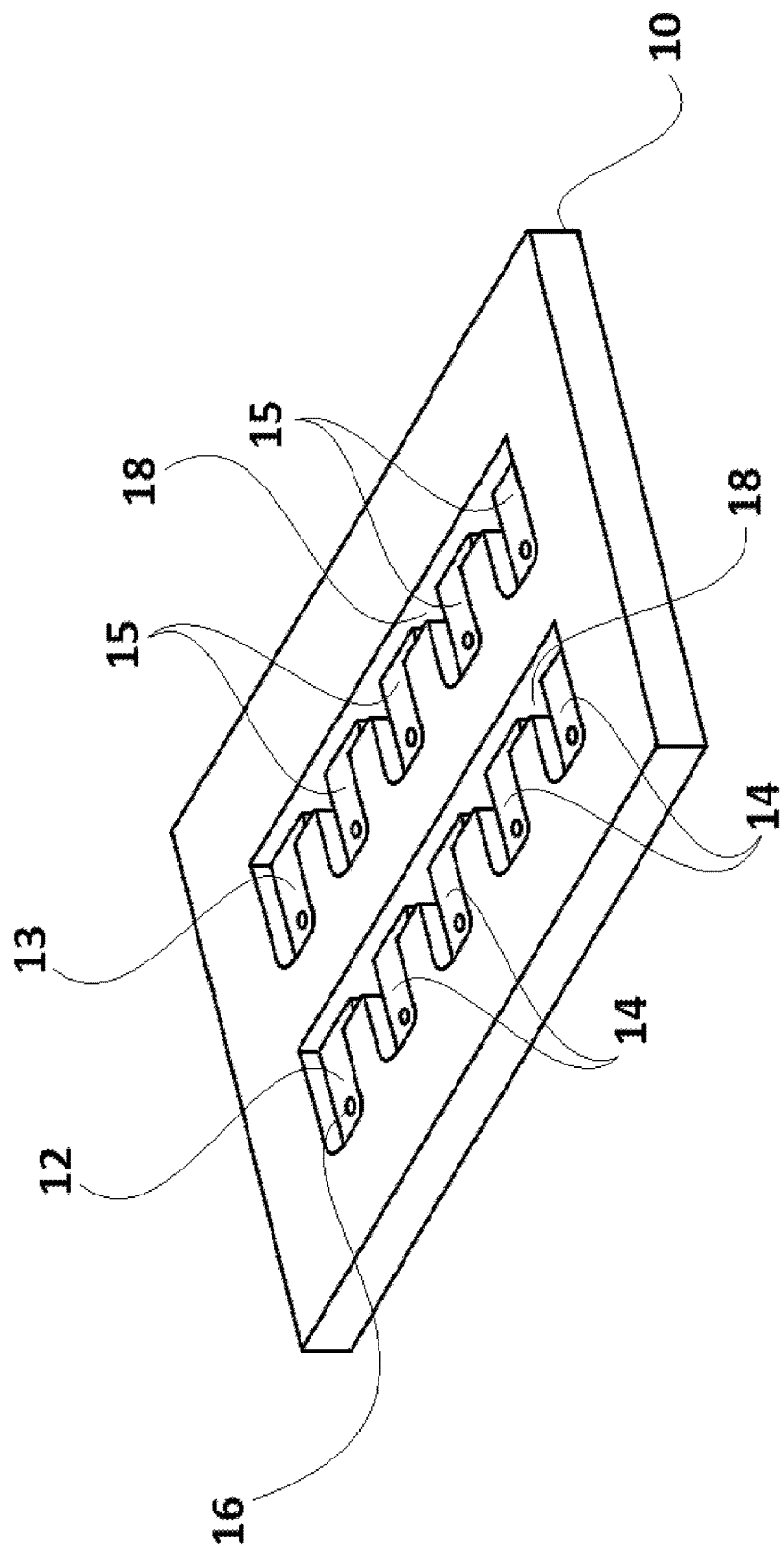
FIG. 5A illustrates a perspective view of an assay cartridge base used in the invention.
Figures 5B, 5C:
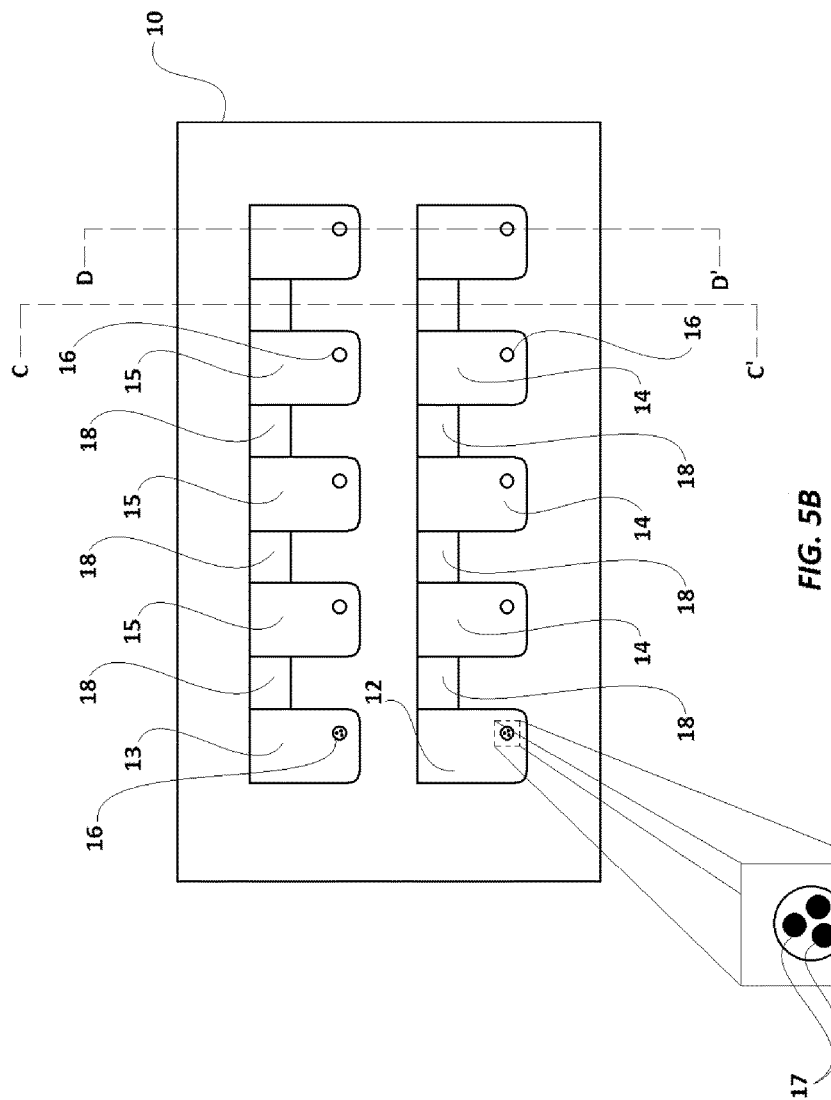
FIG. 5B illustrates a plan view of the assay cartridge base of FIG. 5A having microbeads in mini-wells 16 of each of wells 12 and 13.
FIG. 5C illustrates a magnified plan view of a mini-well 16 of the assay cartridge base of FIG. 5B, having magnetic microbeads therein.
Figure 5D:
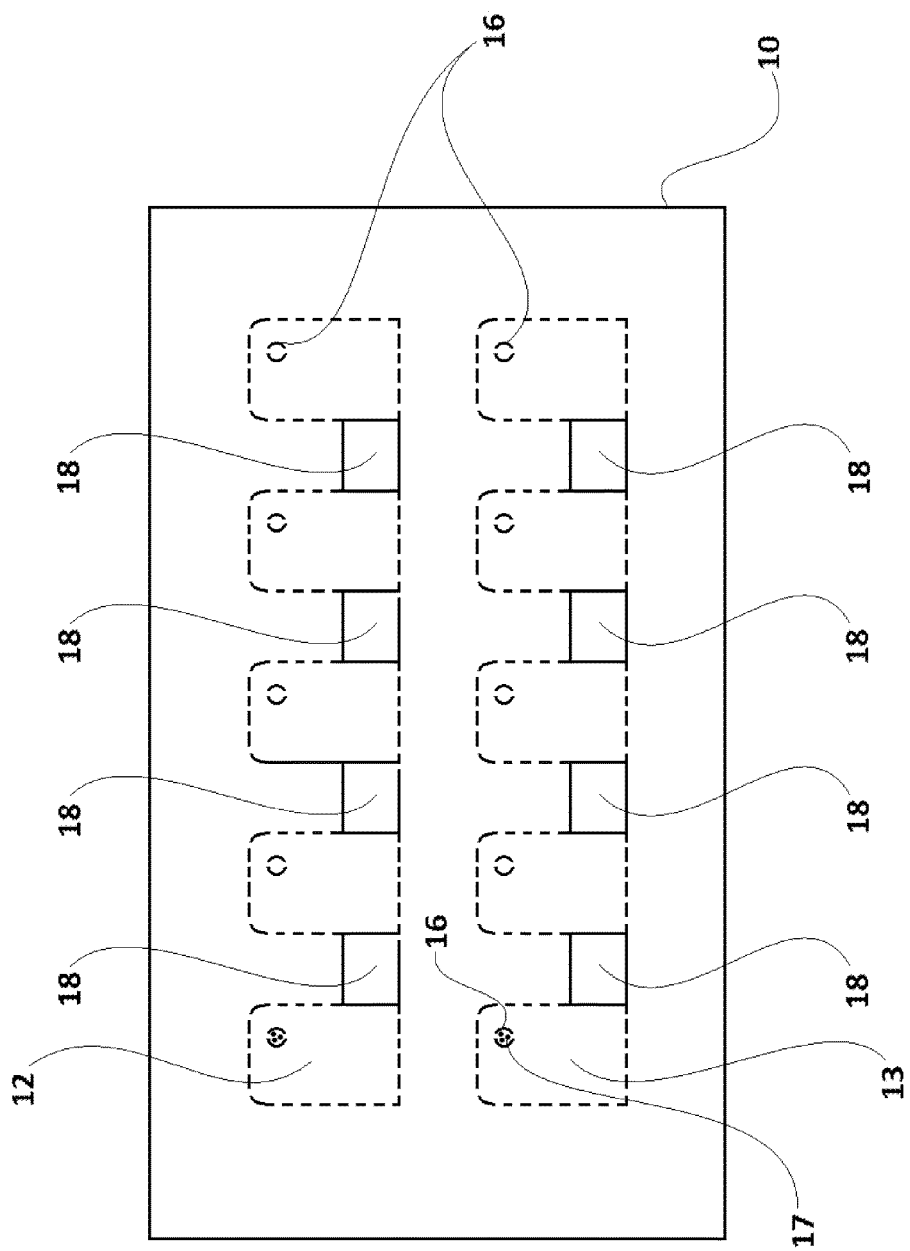
FIG. 5D illustrates a plan view following inversion of the assay cartridge base of FIG. 5A.
Figure 5E:
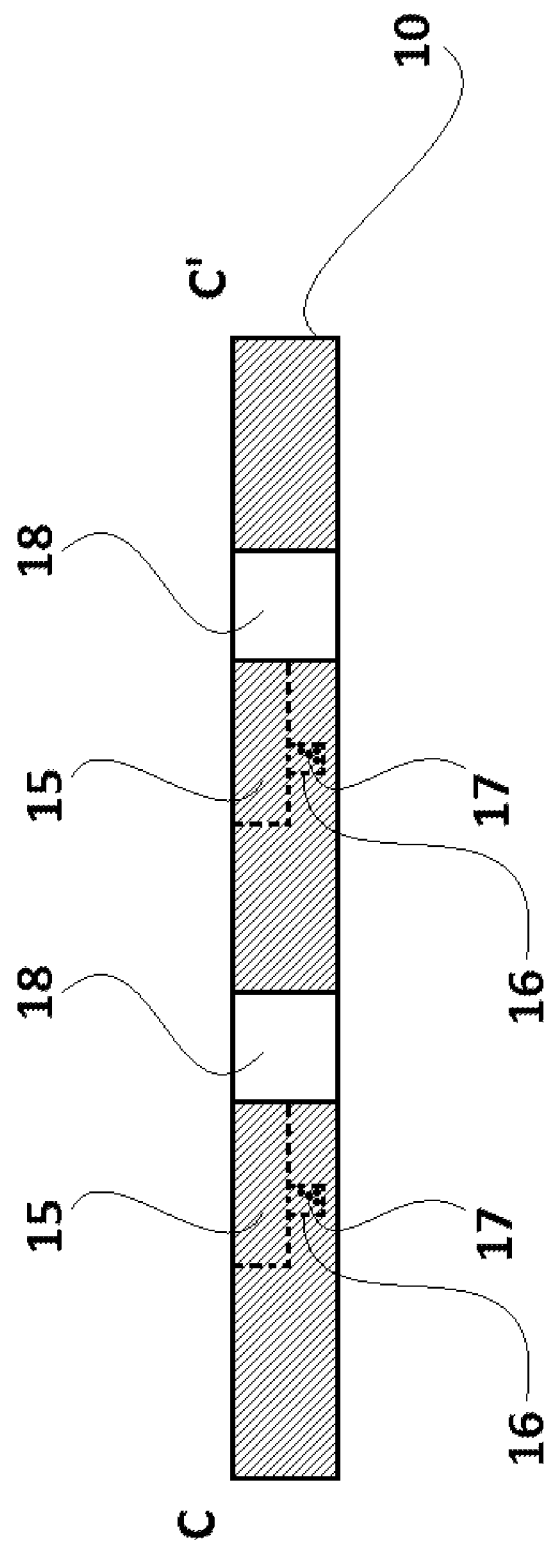
FIG. 5E illustrates a cross-sectional view of assay cartridge base of FIG. 5B taken along lines C-C'.
Figure 6A:
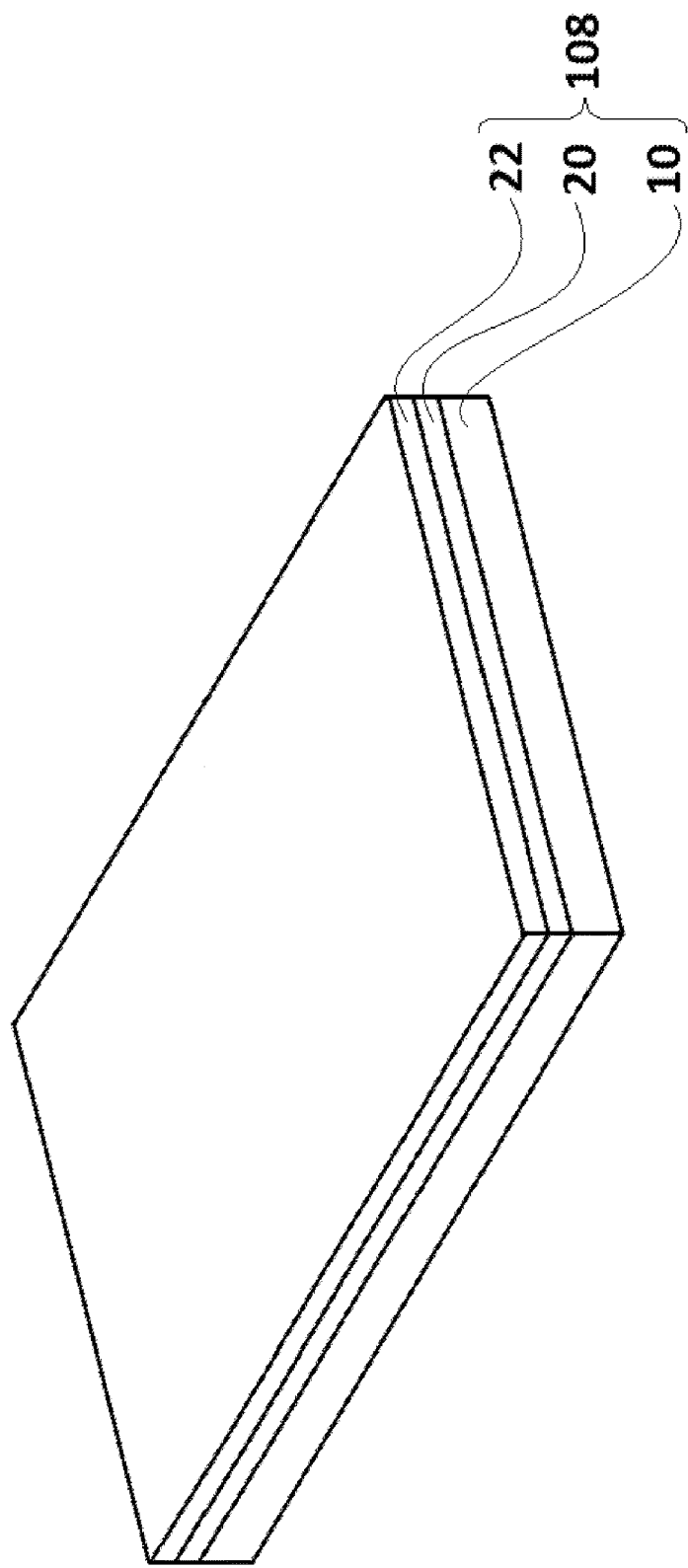
FIG. 6A illustrates an embodiment of an assay cartridge having a protective cover layer.
Figure 6B:
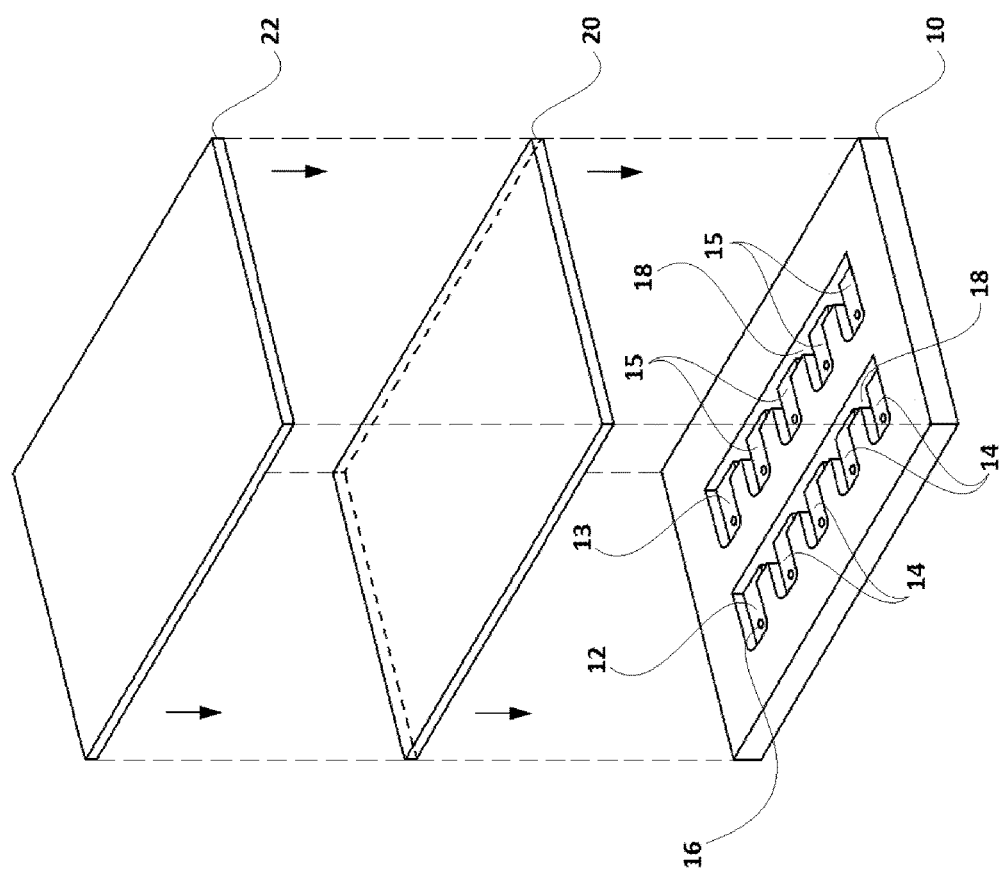
FIG. 6B illustrates an exploded, elevational view of a first layer and a cover for the assay cartridge herein.
Figure 6C:
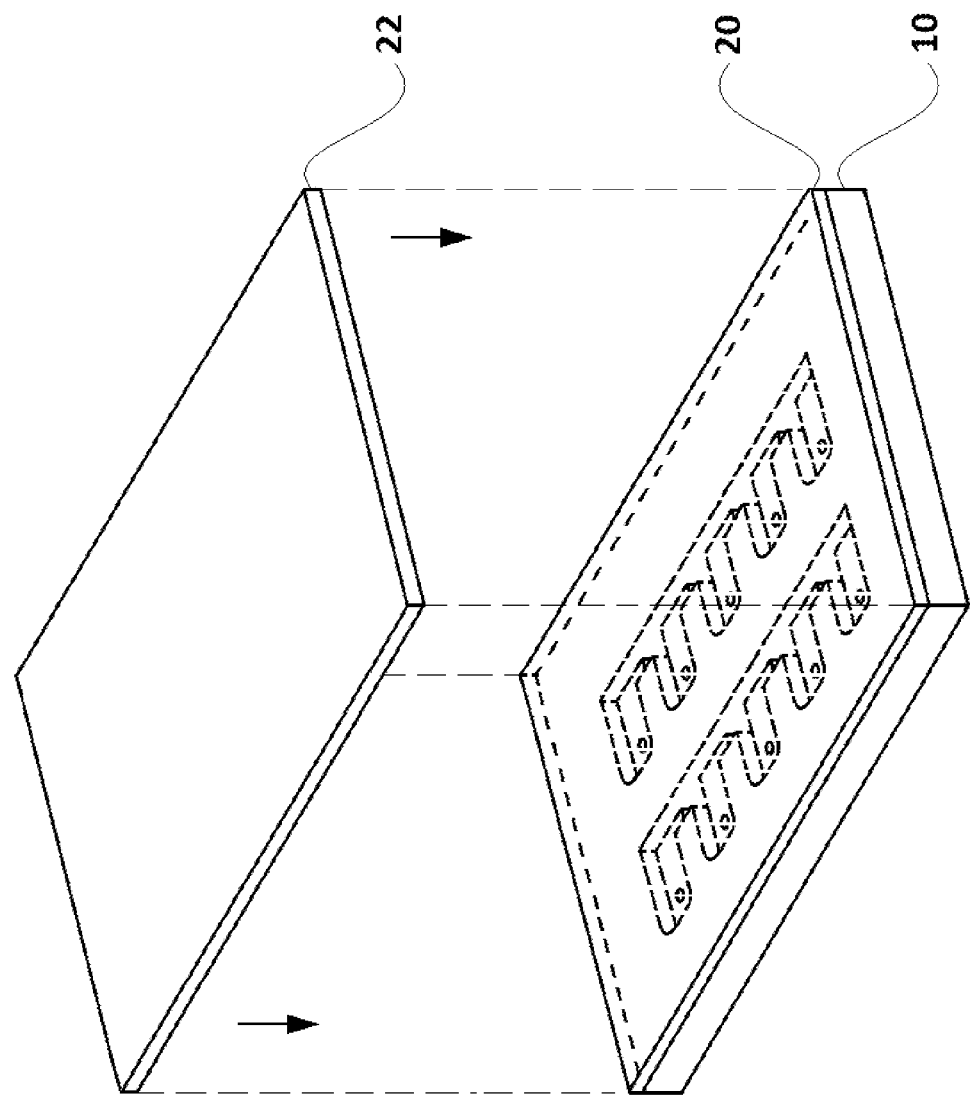
FIG. 6C illustrates an elevational view of the assay cartridge with the first layer in place and the cover exploded.
Figure 6E:
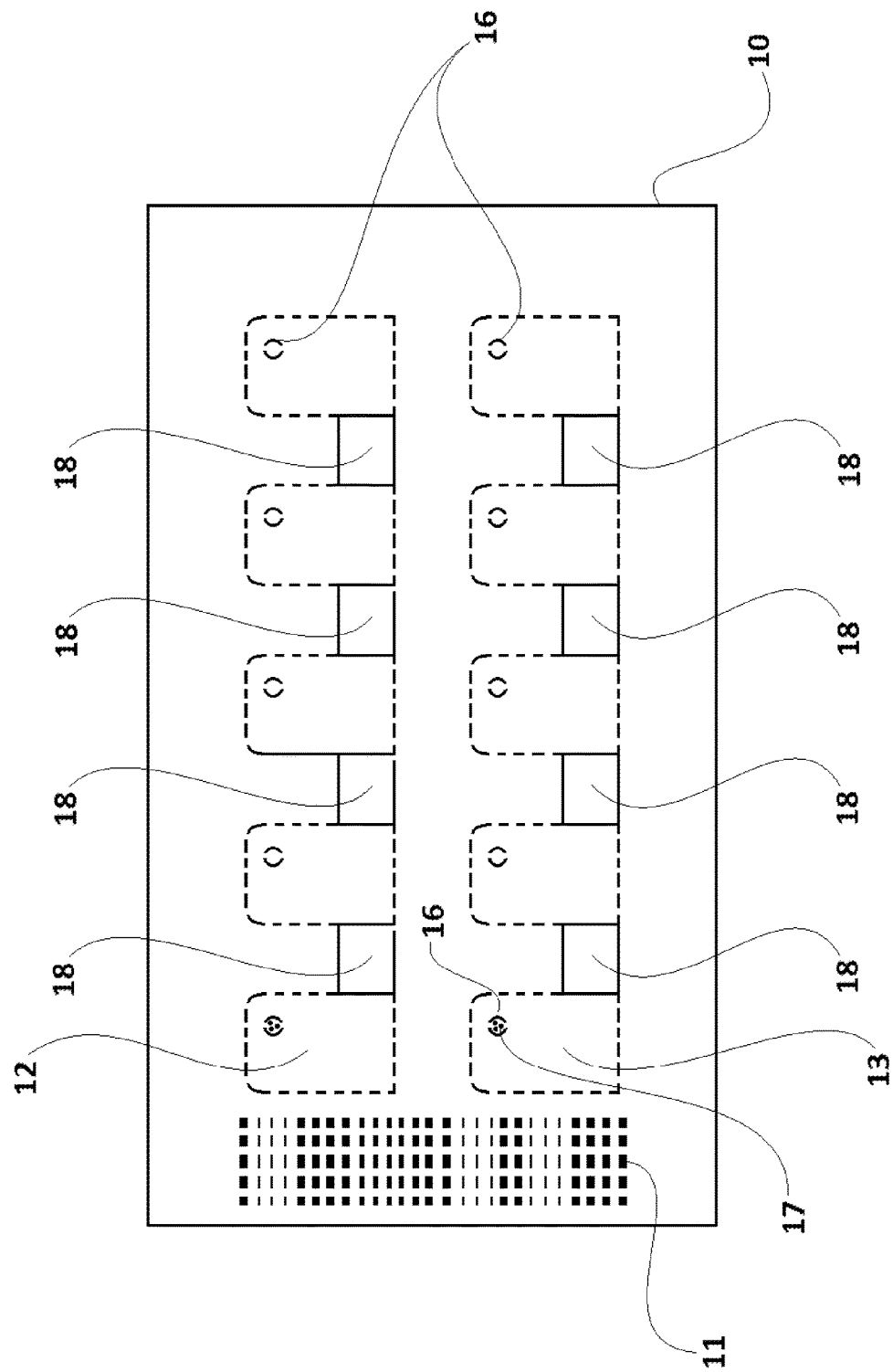
FIG. 6E illustrates a plan view following inversion of the assay cartridge with the first layer and the cover in place.
Figure 6F:
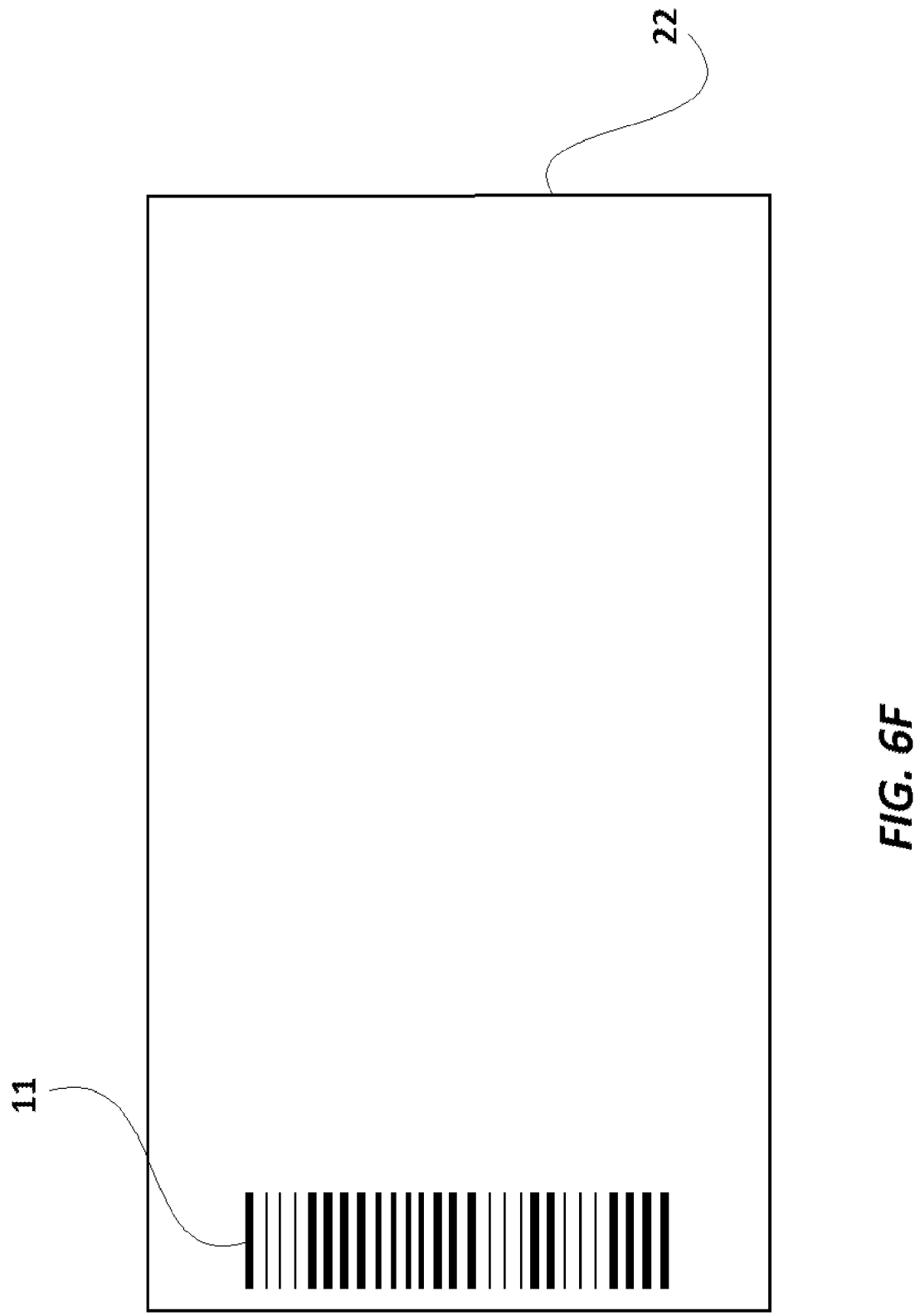
FIG. 6F illustrates a plan view of the inner side of the cover.

As illustrated in FIGS. 4A and 4B, magnet carrier base 138 includes two identical spherical scanning magnets 218 and two cylindrical orienting magnets 220. Each orienting magnet 220 is placed vertically in alignment below its corresponding scanning magnet 218. Orienting magnets 220 help align the poles of scanning magnets 218 in the same direction as the poles of orienting magnets 220. The magnet carrier base 138 is made of a polymer (such as high-density polyethylene ("HDPE")). Each scanning magnet 218 and corresponding orienting magnet 220 is held in a well provided on the upper surface of magnet carrier base 138.

The microcomputer 142 can vary the voltage at third output port 180 and thus the amount of attractive force exerted by solenoid 132, to induce varying degrees of electromagnetic force pulling shaft 134 into solenoid 132. On being energized by flow of DC current through its coil by application of potential difference across rods 128 and 130 (i.e. by enabling third output port 180 at a voltage levels between 2-9V), the electromagnetic force generated by solenoid 132 pulls varying length of the solenoid shaft 134 into the solenoid 132. As the solenoid shaft 134 is pulled into the solenoid 132, the magnet carrier base 138 moves closer to the solenoid 132 and the spring 136 gets compressed. On removal or lowering of the potential difference applied across rods 128 and 130 (done by disabling or lowering the voltage at third output port 180, and hence lowering of electric current through the solenoid 132) spring 136 releases and pushes magnet carrier base 138 away from the solenoid 132, thus pushing out the solenoid shaft 134, whereby it returns to its default position. The direction of longitudinal displacement of the solenoid shaft 134 and the magnet carrier base 138 is preferably perpendicular to the axis 192. Preferably, axis 192 and axis 216 are both parallel to the plane of the scanning platform 106. Scanning platform 106 is positioned on the scanner cover 102 to preferably be intersected by axis 192.

The two-dimensional space covered by magnet carrier base 138 along axis 192 and 216, under the scanning platform 106, is kept sufficiently large so that the magnet carrier base 138 can be moved under the scanning platform 106 over most of the surface of assay cartridge 108. The dimensions of the driving box 104 and all components included within are chosen suitably to facilitate two-dimensional movement of magnet carrier base 138.

Based on the type of assay performed and the type of assay cartridge 108, the microcomputer 142 can be programmed/instructed to guide movement of magnet carrier base 138 within permitted two-dimensional space defined by axis 192 and axis 216 under the scanning platform 106. While the DC motor can be driven to move the magnet carrier base 138 along axis 192, the solenoid 132 can move magnet carrier base 138 along axis 222 when actuated.

Assay cartridge 108 used in the current embodiment is shown in FIGS. 5A-6G. Assay cartridge base 10 is preferably made of a transparent polystyrene, polytetrafluoroethylene ("Teflon®") or polyethylene, and has two rows of a series of wells, with the first well in each row labeled as 12 and 13, respectively, and the remaining wells in one row designated 14, and the remaining wells in the other row designated 15. Each well (12, 13, 14, 15) also has a mini-hole 16 which extends through the cartridge 108 in its corner, as best seen in FIGS. 5A-5G. Assay cartridge base 10 also has a series of channels 18, which extend completely through the cartridge 10, and separate each well (12, 13, 14, 15) from the well next to it. As shown in FIGS. 6A and 6C, a transparent or translucent layer 20 (preferably a translucent plastic paraffin film, including but not limited to Parafilm® and similar products, which are transparent or translucent and can adhere to cartridge base 10) covers and seals the wells (12, 13, 14, 15). Layer 20 adheres to the portions of cartridge base 10 between the wells (12, 13, 14, 15) and channels 18, to seal the contents of the wells (12, 13, 14, 15), and to seal one side of the channels 18 from the surroundings. Cover 22, as illustrated in FIG. 6A-6C is designed to protect layer 20, especially during transport, and is preferably made of paper or a polymer. The covering layer 22 also carries a barcode 11 (provided on the surface of the cover 22 which is laid over layer 20). The barcode 11 provides a unique identification code to the assay cartridge 108. It is to be noted that in some alternate embodiments, instead of being on the cover 22, the barcode 11 may be provided on the layer 20, or directly upon cartridge base 10

In one example of an Enzyme-Linked Immunosorbent (ELISA) assay ran with assay device 100, sample solution is introduced into the well adjacent to well 12 and a control solution is introduced into well 13. Preferably, the sample is placed into the mini-holes 16 in the designated well 14. Magnetic beads 17 coated with antibody against antigens in the control solution (and which may target antigens in the sample, if the sample is positive) are also placed into wells 12 and 13.

Reagents for other steps in the assay (e.g., solutions of labeled secondary antibodies which target and bind to the antigens; solutions to develop the labels on the secondary antibodies into discernable colors) are loaded through mini-holes 16 of other wells 14 and 15. These reagents are placed in wells 14 and 15 in a series such that the requisite assay steps are performed as the magnetic beads are moved from wells 12 and 13 and through the series of wells 14 and 15.

The wells (12, 13, 14, 15) are then sealed with layer 20, and preferably, layer 20 is covered by cover 22. Prior to using cartridge 108 in an assay, the barcode 11 is scanned (can be by the scanner included in the scanner cover 102 or can be done manually by the user) and the scanned barcode information is sent to a server/website, which identifies the assay type and provides the instructions about the assay steps and their timing (preferably over the internet) to microcomputer 142 (preferably through transceiver 182). Alternatively, the instructions can be retrieved from the server/website and manually input or electronically fed into microcomputer 142 (through means such as the Keyboard 107 or otherwise using flash drives via USB ports, not illustrated in figures).

Cartridge 108 is inverted and placed into scanning platform 106 (with the sealed side, i.e., the layer 20 side, facing down, and the edge of the assay cartridge 108 near wells 12 and 13 towards the keyboard 107), as shown in FIG. 1. From there, the components in driving box 104 are actuated by the instructions (from keyboard 107 and/or microcomputer 142) to perform the assay steps in the correct sequence. For example, DC motor 122 is actuated for sufficient time to drive movement of magnet carrier base 138 such that scanning magnets 218 move from their first position (directly below each of wells 12 and 13) to the second position, below the next wells 14, 15 in the series—and then to a third position, below the wells 14, 15 in the series which each contain a solution of labeled secondary antibodies. Magnetic beads 17 are thereby dragged by magnetic attraction to scanning magnets 218 along the inner side of layer 20 through the nearest channel 18, and into the respective next well 14 or 15 in the series.

Optionally, solenoid 132 can be alternately actuated and de-energized to move magnet carrier base 138 vigorously back and forth along axis 216 to mix the magnetic beads with the solutions in wells 12, 13, 14, 15, any time mixing of well contents and beads is desired. Rather than spring 136, another type of passive return mechanism, including an elastic band, may be used to return base 138 to its resting position, before another potential is applied. Another coil could also be used to effect such return.

DC motor 122 is next actuated for sufficient time to drive movement of magnet carrier base 138 such that scanning magnets 218 move from their third position to a fourth position, below the next wells 14, 15 in the series—which each contain a development solution for the label. A well 15 with the development solution should show color once magnetic beads 17 arrive therein (because it includes the control), and the well in row 14 with the development solution should show color if it was positive for the antigen targeted by the antibody on magnetic beads 17. Movement of magnet carrier base 138 may also be actuated again, to carry magnetic beads 17 to a well 14, 15 in the series which includes a solution to stop further color development.

In selecting scanning magnets 218 and orienting magnets 220 for the assay device 10, and the manner of movement of base 138, important parameters include:

1. The ability to focus the magnetic field to produce a tight cluster of magnetic beads 17, so that during the assay (see below), the beads 17 move cleanly through the air gaps in channels 18 without excessive scraping against the walls of channels 18.

2. Induce a magnetic field of sufficient strength to pull the magnetic beads 17 when the magnets 218 are moved suddenly back and forth or otherwise to mix the beads 17 with the well reagents, and also to pull the beads 17 in a cluster cleanly through the channel.

3. The strength of the magnetic field acting on magnetic beads 17 should be below a level which moves the beads 17 as a tight cluster during mixing (above), because one wants the bead cluster to spread out a bit (like a comet tail) when the magnetic field moves suddenly, so as to enhance mixing. The magnetic field strength should also be below a level where it would cluster the beads too tightly, cause interference with other magnets/channels, or cause interference with the circuit board (which may be part of the assay driver system). In one embodiment, a neodynium permanent magnet of Br-max of approximately 4500 Gauss may be used.

4. There must be a precise gap between the magnets and the layer 20 (on which beads 17 rest). This is needed in order to produce a known motion patterns for the beads. Cylindrical or other shaped magnets may be preferred to spherical magnets 218, as they enable more precise control over the clearance between magnets 218 and the layer 20.

The next step is scanning of the wells 14 and 15 which show color, to confirm the assay is functioning properly (specific wells 15 show color change), and if there was a positive result (based on whether the specific wells 14 shows color change). A sensor which reads overall light intensity (and/or with color filters) may be used to show the color change.

The relative antigen concentration in the sample may also be determined, based on the degree of color change—where the wells with solution to stop further color change are provided. Preferably, the sensor results or the scanned images are captured through scanner included in scanning platform 106 and are transmitted to the server/website for interpretation through transceiver 182 (or manually by storing them in flash memories and uploading to a server), and/or to another authorized recipient or health care provider, and/or to the patient. The scanning and transmission of the sensor results or image can be automatically performed on the assay cartridge 108 by inverting it (so the well contents are visible from below) in place in scanning platform 106, in accordance with instructions provided to microcomputer 142. Alternatively, a scanner or results sensor can be separated from device 100, and image scanning can be performed outside of device 100.

The assay cartridge 108 described herein is preferably for use with assay device 10, which actuates and controls performance of the assay, and reports results, in a secure remotely authorized system, as described herein. After assay completion, images scanned and representing the assay results are transmitted for interpretation or to the assay subject or his/her designees (including distribution to anyone who can receive the material under applicable HIPPA regulations).

Figure 7:
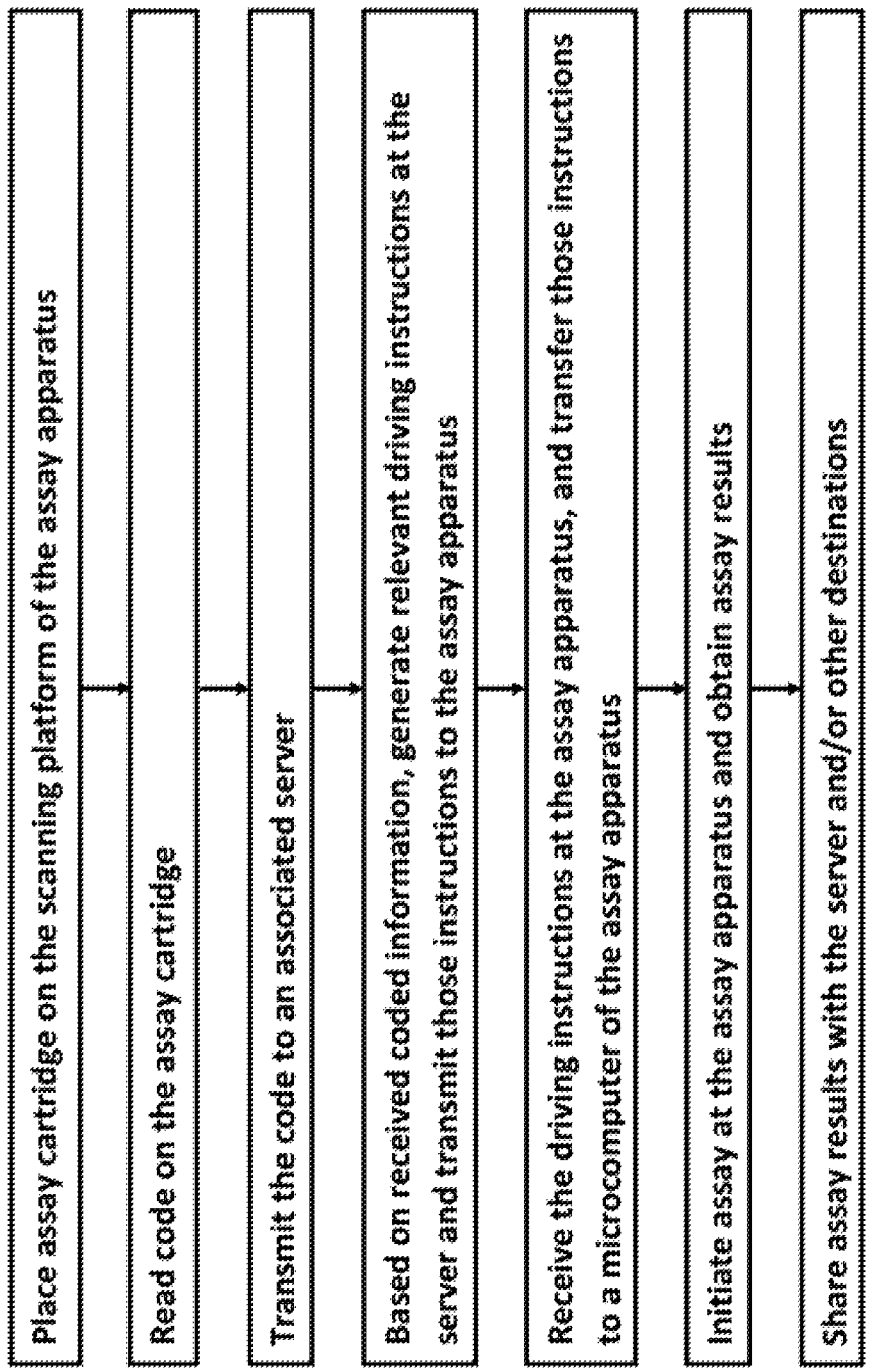
FIG. 7 is a flow diagram of the steps involved in initiating and performing an assay with the assay driving apparatus and the assay cartridge shown and described herein.
Figure 8:
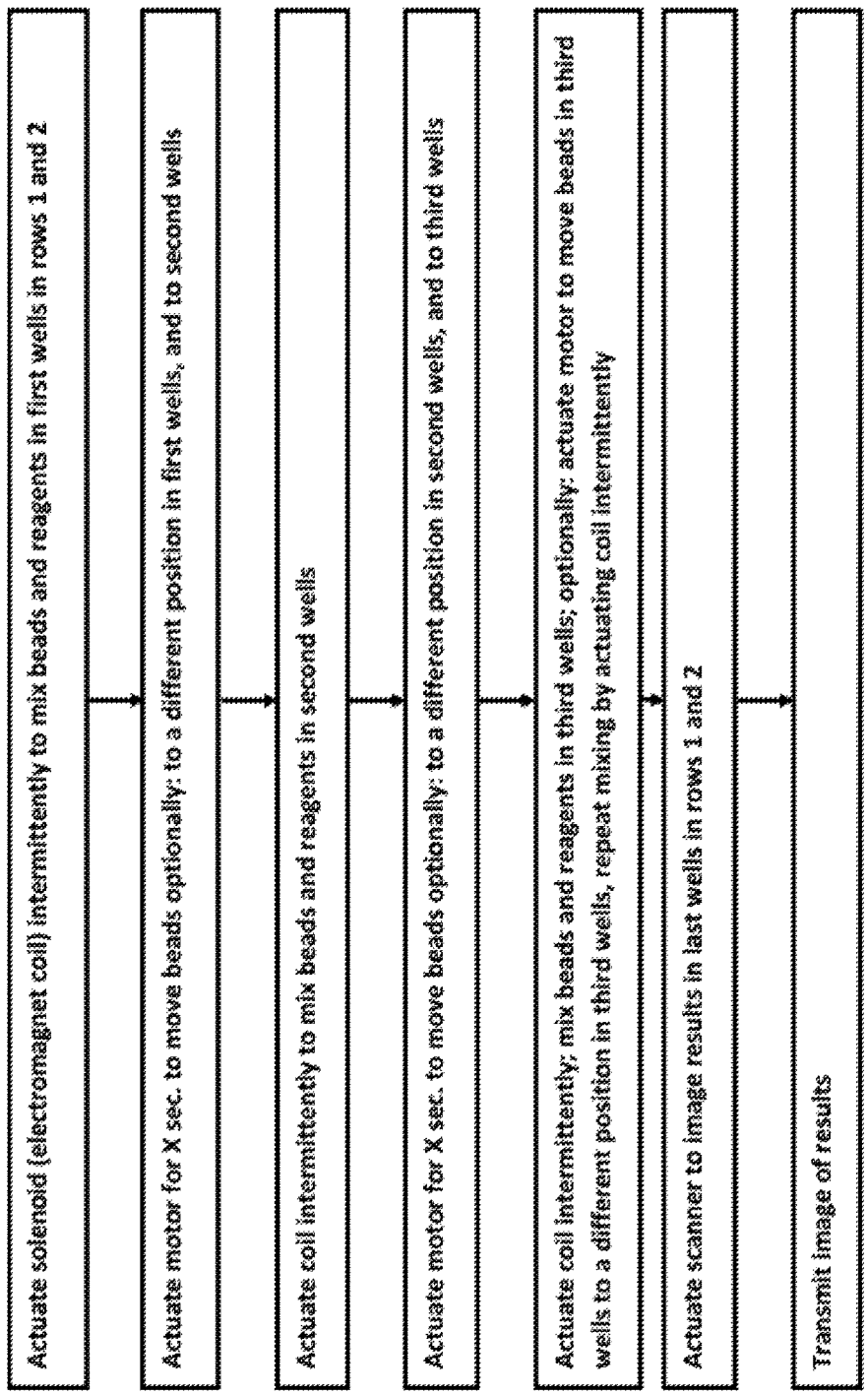
FIG. 8 is a flow diagram of the instructions for initiating and performing an assay with the assay driving apparatus and the assay cartridge shown and described herein.

A flow chart showing the steps of cartridge identification through assay imaging and transmission is shown in FIG. 7. A flow chart exemplifying the instructions executed by microcomputer 142 is shown in FIG. 8. The steps in FIG. 7 of transmitting the barcode and transmitting instructions can be wireless, through phone lines, or through the internet, or by any other means. The assay steps described above and the reagents and beads in various wells would be different in different assays and assay formats. The device 100 and system described herein is appropriate for use with any assay where magnetic beads can be used.

Example 1: Performing an ELISA Immunoassay

After cartridge 10 is loaded with magnetic antibody-coated beads 17 and reagents suitable for an ELISA, sample is added to well 12, and a control is added to well 13. The instructions are executed to induce assay driver to move unit 138 such that the antibody-coated beads 17 are moved through channels 18 and to the next well 14, 15, respectively. The antibody coating on beads 17 binds to reactive antigens in the sample or control which reactive antigens are then carried by beads 17.

Oscillating movement of unit 138 in a direction the same, different or transverse to the direction of travel induces mixing of beads 17 with the contents of the wells in which they reside. The mixing can be carried out in certain wells, or in all wells in the series.

It is preferred that the adjustment of the strength of the magnetic field acting on magnetic beads 17 and the acceleration and deceleration of unit 138 is adjusted so that the beads 17 spread out somewhat (like a comet tail) when unit 138 moves to take the beads 17 to the next well, or when oscillating unit 138 to mix beads with the well contents. Rapid acceleration and deceleration of unit 138 is therefore preferred.

The next wells 14, 15, in the series are loaded with secondary antibodies carrying enzyme, or preferably, also with tertiary antibodies carrying enzyme. Ultimately, beads 17 are moved to wells 14, 15 containing the substrate for the enzyme carried by the secondary or tertiary antibodies, which induces a detectable color change. The color change can be accomplished with an enzyme substrate combination. In such case, the wells where there is a color change may contain one of the following: PNPP (p-Nitrophenyl Phosphate), ABTS (2,2'-Azinobis [3-ethylbenzothiazoline-6-sulfonic acid]-diammonium salt), OPD (o-phenylenediamine dihydrochloride), or TMB (3,3',5,5'-tetramethylbenzidine)]. One suitable enzyme-substrate combination is horseradish peroxidase (HRP) as the enzyme and TMB as the detection substrate. When using chemiluminescent chemicals and HRP, which is another option, light is generated as well as a color change.

Some wells 14, 15 may optionally serve as wash chambers to remove contaminants attached non-specifically to the beads 17—although contaminants on beads 17 are also removed by passage through the air gaps in channels 18. Oscillating movement of unit 138 in a direction transverse to the direction of travel induces mixing of beads 17 with the contents of wells which contain wash reagents—when the beads 17 reside in those wells.

After a suitable reaction time (for example, 2-10 minutes) the beads 17 are moved to final wells 14, 15, containing reagents to terminate the enzyme-substrate reaction and stop the color change from progressing further. The concentration of analyte in sample or control solution is proportional to the amount of the analyte that gets attached to the antibody-coated magnetic particles, which in turn is proportional to the number of secondary antibody molecules that get attached to the analyte. Because the secondary or tertiary antibodies are attached to HRP, the quantity of secondary or tertiary antibodies bound to HRP governs the rate of catalytic breakdown of TMB.

The color concentration can be quantified with a light source and detector, for example. The final wells can have results recorded or be scanned and imaged, and the image or results can be transmitted for remote analysis of the assay results, or to the patient or a designated recipient, as described further below. A suitable scanner for generating the assay well images is a four channel photoelectric color sensor, capable of sensing the clear polymer and up to three more colors.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An apparatus for performing an assay where magnetic beads are moved through a plurality of wells which contain assay reagents, comprising:
   an assay cartridge having a plurality of wells containing assay reagents, and wherein at least one well contains magnetic beads;
   scanning magnets held in a base which is movable with respect to the assay cartridge along a first axis and a second axis, wherein said first axis intersects the second axis, such that movement of the base along the first axis causes the magnetic beads to move from one well to another;
   at least two rods extend into the base, the base sliding on the rods to move along the first axis, wherein the rods are in electrical contact with a coil which, upon actuation by a processor configured to selectively apply a potential to the rods from a power source in electrical connection with the rods, oscillates the base along the second axis.

2. The apparatus of claim 1, wherein the rods are connected with the base with brushes, wires or a combination of the two.

3. The apparatus of claim 1, wherein the electrical potential of one of the rods is higher than the electrical potential of another rod.

4. The apparatus of claim 1, wherein the first axis is transverse to the second axis.

5. The apparatus of claim 1, wherein movement of said base along the first axis is motor-powered by rotation of an externally threaded shaft parallel to the first axis and extending into a matingly threaded portion of the base.

6. The apparatus of claim 1, wherein the assay cartridge has two parallel rows of wells and the base holds at least two scanning magnets.

7. The apparatus of claim 6, further including at least two substantially cylindrical orienting magnets, each positioned to magnetically interact with one of the scanning magnets.

8. The apparatus of claim 1, wherein the power source supplies DC to the rods but is connected with an AC initial source.

9. The apparatus of claim 5, wherein the processor controls intervals of rotation of the externally threaded shaft.

10. The apparatus of claim 1, further including a scanner which can scan and record data representing assay results from at least one well of the assay cartridge.

11. The apparatus of claim 10, further including a transmitter which can transmit said data to a remote location.

12. An apparatus for performing an assay where magnetic beads are moved through a plurality of wells which contain assay reagents, comprising:
    an assay cartridge having a plurality of wells containing assay reagents, and wherein at least one well contains magnetic beads;
    scanning magnets and orienting magnets positioned in a base and located a specific distance from the assay cartridge;
    said base being movable with respect to the assay cartridge along a first axis and a second axis, wherein said first axis intersects the second axis, such that movement of the base along the first axis causes the magnetic beads to move through first channels in the assay cartridge from one well to another;
    at least two rods extend into the base, the base sliding on the rods to move along the first axis, wherein the rods are in electrical contact with a coil which, upon actuation, oscillates the base along the second axis using a spring which is compressed upon the coil being actuated; and
    a power source and a processor in electrical connection with the rods, the processor configured to apply a potential to the rods which actuates the coil.

13. The apparatus of claim 12, wherein the first axis is transverse to the second axis.

14. The apparatus of claim 12, wherein movement of said base along the first axis is powered by motor-driven rotation of an externally threaded shaft parallel to the first axis and extending into a matingly threaded portion of the base.

15. The apparatus of claim 12, wherein there are two parallel rows of wells and the base holds at least two scanning magnets.

16. The apparatus of claim 12, wherein the wells are separated by air gaps, formed by second channels extending into the cartridge, and transverse to the first channels.

17. The apparatus of claim 15, wherein there are at least two substantially cylindrical orienting magnets, wherein the orienting magnets are further from the cartridge than the scanning magnets.

18. The apparatus of claim 14, further including a microcomputer which controls intervals of rotation of the externally threaded shaft and/or the intervals of potentials provided to the rods.

19. The apparatus of claim 12, further including a scanner which can scan and record data representing assay results from at least one well of the assay cartridge.

20. The apparatus of claim 19, further including a transmitter which can transmit said data to a remote location.

* * * * *